United States Patent
Badower

(10) Patent No.: US 9,320,450 B2
(45) Date of Patent: Apr. 26, 2016

(54) METHODS AND APPARATUS TO GATHER AND ANALYZE ELECTROENCEPHALOGRAPHIC DATA

(71) Applicant: Yakob Badower, Frankfurt am Main (DE)

(72) Inventor: Yakob Badower, Frankfurt am Main (DE)

(73) Assignee: The Nielsen Company (US), LLC, New York, NY (US)

( * ) Notice: Subject to any disclaimer, the term of this patent is extended or adjusted under 35 U.S.C. 154(b) by 466 days.

(21) Appl. No.: 13/829,849

(22) Filed: Mar. 14, 2013

(65) Prior Publication Data

US 2014/0276183 A1    Sep. 18, 2014

(51) Int. Cl.
*A61B 5/04* (2006.01)
*A61B 5/0476* (2006.01)
*A61B 5/00* (2006.01)

(52) U.S. Cl.
CPC ............. *A61B 5/0476* (2013.01); *A61B 5/6803* (2013.01); *A61B 5/6831* (2013.01); *A61B 2562/04* (2013.01)

(58) Field of Classification Search
CPC .. A61B 5/0476; A61B 5/0478; A61B 5/4064; A61B 5/4806; A61B 5/4821; A61B 5/6803; A61B 5/6814; A61B 5/6831; A61B 2503/12; A61B 2560/0443; A61B 2560/0468; A61B 2562/0209; A61B 2562/04; A61B 2562/046; A61B 2562/22; A61B 2562/225
USPC ......... 600/372, 382, 383, 390, 393, 544–545; 439/38–40, 909, 289, 291
See application file for complete search history.

(56) References Cited

U.S. PATENT DOCUMENTS

| | | |
|---|---|---|
| 2,409,033 A | 10/1946 | Garceau |
| 2,549,836 A | 4/1951 | McIntyre et al. |
| 3,490,439 A | 1/1970 | Rolston |
| 3,572,322 A | 3/1971 | Wade |
| 3,735,753 A | 5/1973 | Pisarski |
| 3,880,144 A | 4/1975 | Coursin et al. |
| 3,901,215 A | 8/1975 | John |
| 3,998,213 A | 12/1976 | Price |
| 4,033,334 A | 7/1977 | Fletcher et al. |

(Continued)

FOREIGN PATENT DOCUMENTS

| | | |
|---|---|---|
| CN | 102791194 | 11/2012 |
| DE | 102010005551 | 7/2011 |

(Continued)

OTHER PUBLICATIONS

Unknown "Promotional Rubber Magnet Clip Holder, Buy Rubber Magnet Clip Holder Promotion Products at Low Price" on Alibaba.com (2015).*

(Continued)

*Primary Examiner* — Lee S Cohen
*Assistant Examiner* — Erin M Cardinal
(74) *Attorney, Agent, or Firm* — Hanley, Flight & Zimmerman, LLC

(57) ABSTRACT

Example apparatus and methods for gathering electroencephalographic signals are disclosed herein. An example apparatus includes a band to be worn on a head of a person and a first strip adjustably coupled to the band. The example apparatus also includes a first set of electrodes coupled to the first strip to gather a first set of signals from the head and a magnetic fastener to couple the first strip to the band.

24 Claims, 13 Drawing Sheets

(56) References Cited

U.S. PATENT DOCUMENTS

| | | | |
|---|---|---|---|
| 4,075,657 A | 2/1978 | Weinblatt | |
| 4,149,716 A | 4/1979 | Scudder | |
| 4,201,224 A | 5/1980 | John | |
| 4,213,463 A | 7/1980 | Osenkarski | |
| 4,279,258 A | 7/1981 | John | |
| 4,397,331 A | 8/1983 | Medlar | |
| 4,411,273 A | 10/1983 | John | |
| 4,417,592 A | 11/1983 | John | |
| 4,537,198 A | 8/1985 | Corbett | |
| 4,557,270 A | 12/1985 | John | |
| 4,610,259 A | 9/1986 | Cohen et al. | |
| 4,613,951 A | 9/1986 | Chu | |
| 4,626,904 A | 12/1986 | Lurie | |
| 4,632,122 A | 12/1986 | Johansson et al. | |
| 4,640,290 A | 2/1987 | Sherwin | |
| 4,683,892 A | 8/1987 | Johansson et al. | |
| 4,695,879 A | 9/1987 | Weinblatt | |
| 4,709,702 A | 12/1987 | Sherwin | |
| 4,736,751 A | 4/1988 | Gevins et al. | |
| 4,755,045 A | 7/1988 | Borah et al. | |
| 4,800,888 A | 1/1989 | Itil et al. | |
| 4,802,484 A | 2/1989 | Friedman et al. | |
| 4,846,190 A | 7/1989 | John | |
| 4,865,038 A | 9/1989 | Rich et al. | |
| 4,885,687 A | 12/1989 | Carey | |
| 4,894,777 A | 1/1990 | Negishi et al. | |
| 4,913,160 A | 4/1990 | John | |
| 4,931,934 A | 6/1990 | Snyder | |
| 4,936,306 A | 6/1990 | Doty | |
| 4,955,388 A | 9/1990 | Silberstein | |
| 4,967,038 A | 10/1990 | Gevins et al. | |
| 4,974,602 A | 12/1990 | Abraham-Fuchs et al. | |
| 4,987,903 A | 1/1991 | Keppel et al. | |
| 5,003,986 A | 4/1991 | Finitzo et al. | |
| 5,010,891 A | 4/1991 | Chamoun | |
| 5,024,235 A | 6/1991 | Ayers | |
| 5,038,782 A | 8/1991 | Gevins et al. | |
| 5,052,401 A | 10/1991 | Sherwin | |
| 5,083,571 A | 1/1992 | Prichep | |
| RE34,015 E | 8/1992 | Duffy | |
| 5,137,027 A | 8/1992 | Rosenfeld | |
| 5,144,952 A * | 9/1992 | Frachet et al. | 600/379 |
| 5,213,338 A | 5/1993 | Brotz | |
| 5,226,177 A | 7/1993 | Nickerson | |
| 5,243,517 A | 9/1993 | Schmidt et al. | |
| 5,273,037 A | 12/1993 | Itil et al. | |
| 5,291,888 A | 3/1994 | Tucker | |
| 5,293,867 A | 3/1994 | Oommen | |
| 5,295,491 A | 3/1994 | Gevins | |
| 5,339,826 A | 8/1994 | Schmidt et al. | |
| 5,345,934 A | 9/1994 | Highe et al. | |
| 5,355,883 A | 10/1994 | Ascher | |
| 5,357,957 A | 10/1994 | Itil et al. | |
| 5,363,858 A | 11/1994 | Farwell | |
| 5,392,788 A | 2/1995 | Hudspeth | |
| 5,406,956 A | 4/1995 | Farwell | |
| 5,406,957 A | 4/1995 | Tansey | |
| 5,447,166 A | 9/1995 | Gevins | |
| 5,450,855 A | 9/1995 | Rosenfeld | |
| 5,452,718 A | 9/1995 | Clare et al. | |
| 5,474,082 A | 12/1995 | Junker | |
| 5,479,934 A | 1/1996 | Imran | |
| 5,513,649 A | 5/1996 | Gevins et al. | |
| 5,518,007 A | 5/1996 | Becker | |
| 5,537,618 A | 7/1996 | Boulton et al. | |
| 5,579,774 A | 12/1996 | Miller et al. | |
| 5,601,090 A | 2/1997 | Musha | |
| 5,617,855 A | 4/1997 | Waletzky et al. | |
| 5,645,577 A | 7/1997 | Froberg et al. | |
| 5,649,061 A | 7/1997 | Smyth | |
| 5,655,534 A | 8/1997 | Ilmoniemi | |
| 5,676,138 A | 10/1997 | Zawilinski | |
| 5,692,906 A | 12/1997 | Corder | |
| 5,697,369 A | 12/1997 | Long, Jr. et al. | |
| 5,720,619 A | 2/1998 | Fisslinger | |
| 5,724,987 A | 3/1998 | Gevins et al. | |
| 5,729,205 A | 3/1998 | Kwon | |
| 5,736,986 A | 4/1998 | Sever, Jr. | |
| 5,740,035 A | 4/1998 | Cohen et al. | |
| 5,740,812 A | 4/1998 | Cowan | |
| 5,762,611 A | 6/1998 | Lewis et al. | |
| 5,771,897 A | 6/1998 | Zufrin | |
| 5,772,591 A | 6/1998 | Cram | |
| 5,774,591 A | 6/1998 | Black et al. | |
| 5,787,187 A | 7/1998 | Bouchard et al. | |
| 5,788,648 A | 8/1998 | Nadel | |
| 5,800,351 A | 9/1998 | Mann | |
| 5,812,642 A | 9/1998 | Leroy | |
| 5,817,029 A | 10/1998 | Gevins et al. | |
| 5,848,399 A | 12/1998 | Burke | |
| 5,868,670 A | 2/1999 | Randell | |
| 5,945,863 A | 8/1999 | Coy | |
| 5,954,642 A | 9/1999 | Johnson et al. | |
| 5,961,332 A | 10/1999 | Joao | |
| 5,983,129 A | 11/1999 | Cowan et al. | |
| 5,983,214 A | 11/1999 | Lang et al. | |
| 6,001,065 A | 12/1999 | DeVito | |
| 6,002,957 A | 12/1999 | Finneran | |
| 6,021,346 A | 2/2000 | Ryu et al. | |
| 6,052,619 A | 4/2000 | John | |
| 6,099,319 A | 8/2000 | Zaltman et al. | |
| 6,120,440 A | 9/2000 | Goknar | |
| 6,128,521 A | 10/2000 | Marro et al. | |
| 6,154,669 A | 11/2000 | Hunter et al. | |
| 6,155,927 A | 12/2000 | Levasseur et al. | |
| 6,161,030 A | 12/2000 | Levendowski et al. | |
| 6,170,018 B1 | 1/2001 | Voll et al. | |
| 6,171,239 B1 | 1/2001 | Humphrey | |
| 6,173,260 B1 | 1/2001 | Slaney | |
| 6,175,753 B1 | 1/2001 | Menkes et al. | |
| 6,228,038 B1 | 5/2001 | Claessens | |
| 6,233,472 B1 | 5/2001 | Bennett et al. | |
| 6,236,885 B1 | 5/2001 | Hunter et al. | |
| 6,254,536 B1 | 7/2001 | DeVito | |
| 6,259,889 B1 | 7/2001 | LaDue | |
| 6,280,198 B1 | 8/2001 | Calhoun et al. | |
| 6,286,005 B1 | 9/2001 | Cannon | |
| 6,289,234 B1 | 9/2001 | Mueller | |
| 6,292,688 B1 | 9/2001 | Patton | |
| 6,301,493 B1 | 10/2001 | Marro et al. | |
| 6,309,342 B1 | 10/2001 | Blazey et al. | |
| 6,315,569 B1 | 11/2001 | Zaltman | |
| 6,322,368 B1 | 11/2001 | Young et al. | |
| 6,330,470 B1 | 12/2001 | Tucker et al. | |
| 6,334,778 B1 | 1/2002 | Brown | |
| 6,349,231 B1 | 2/2002 | Musha | |
| 6,374,143 B1 | 4/2002 | Berrang et al. | |
| 6,381,481 B1 | 4/2002 | Levendowski et al. | |
| 6,398,643 B1 | 6/2002 | Knowles et al. | |
| 6,422,999 B1 | 7/2002 | Hill | |
| 6,425,764 B1 | 7/2002 | Lamson | |
| 6,434,419 B1 | 8/2002 | Gevins et al. | |
| 6,453,194 B1 | 9/2002 | Hill | |
| 6,481,013 B1 | 11/2002 | Dinwiddie et al. | |
| 6,487,444 B2 | 11/2002 | Mimura | |
| 6,488,617 B1 | 12/2002 | Katz | |
| 6,510,340 B1 | 1/2003 | Jordan | |
| 6,520,905 B1 | 2/2003 | Surve et al. | |
| 6,545,685 B1 | 4/2003 | Dorbie | |
| 6,574,513 B1 | 6/2003 | Collura et al. | |
| 6,575,902 B1 | 6/2003 | Burton | |
| 6,577,329 B1 | 6/2003 | Flickner et al. | |
| 6,585,521 B1 | 7/2003 | Obrador | |
| 6,594,521 B2 | 7/2003 | Tucker | |
| 6,598,006 B1 | 7/2003 | Honda et al. | |
| 6,606,102 B1 | 8/2003 | Odom | |
| 6,606,519 B1 | 8/2003 | Powell | |
| 6,609,024 B1 | 8/2003 | Ryu et al. | |
| 6,623,428 B2 | 9/2003 | Miller et al. | |
| 6,626,676 B2 | 9/2003 | Freer | |
| 6,648,822 B2 | 11/2003 | Hamamoto et al. | |
| 6,652,283 B1 | 11/2003 | Van Schaack et al. | |
| 6,654,626 B2 | 11/2003 | Devlin et al. | |
| 6,656,116 B2 | 12/2003 | Kim et al. | |

(56) References Cited

U.S. PATENT DOCUMENTS

| | | |
|---|---|---|
| 6,662,052 B1 | 12/2003 | Sarwal et al. |
| 6,665,560 B2 | 12/2003 | Becker et al. |
| 6,678,866 B1 | 1/2004 | Sugimoto et al. |
| 6,688,890 B2 | 2/2004 | von Buegner |
| 6,699,188 B2 | 3/2004 | Wessel |
| 6,708,051 B1 | 3/2004 | Durousseau |
| 6,712,468 B1 | 3/2004 | Edwards |
| 6,754,524 B2 | 6/2004 | Johnson, Jr. |
| 6,757,556 B2 | 6/2004 | Gopinathan et al. |
| 6,788,882 B1 | 9/2004 | Geer et al. |
| 6,792,304 B1 | 9/2004 | Silberstein |
| 6,839,682 B1 | 1/2005 | Blume |
| 6,842,877 B2 | 1/2005 | Robarts et al. |
| 6,904,408 B1 | 6/2005 | McCarthy et al. |
| 6,915,148 B2 | 7/2005 | Finneran et al. |
| 6,950,698 B2 | 9/2005 | Sarkela et al. |
| 6,958,710 B2 | 10/2005 | Zhang et al. |
| 6,961,601 B2 | 11/2005 | Matthews et al. |
| 6,973,342 B1 | 12/2005 | Swanson |
| 6,978,115 B2 | 12/2005 | Whitehurst et al. |
| 6,993,380 B1 | 1/2006 | Modarres |
| 7,035,685 B2 | 4/2006 | Ryu et al. |
| 7,050,753 B2 | 5/2006 | Knutson |
| 7,104,801 B1 * | 9/2006 | Brodnick et al. ............ 439/38 |
| 7,113,916 B1 | 9/2006 | Hill |
| 7,120,880 B1 | 10/2006 | Dryer et al. |
| 7,127,283 B2 | 10/2006 | Kageyama |
| 7,130,673 B2 | 10/2006 | Tolvanen-Laakso et al. |
| 7,150,715 B2 | 12/2006 | Collura et al. |
| 7,164,967 B2 | 1/2007 | Etienne-Cummings et al. |
| 7,173,437 B2 | 2/2007 | Hervieux et al. |
| 7,177,675 B2 | 2/2007 | Suffin et al. |
| 7,194,186 B1 | 3/2007 | Strub et al. |
| 7,222,071 B2 | 5/2007 | Neuhauser et al. |
| 7,272,982 B2 | 9/2007 | Neuhauser et al. |
| 7,286,871 B2 | 10/2007 | Cohen |
| 7,340,060 B2 | 3/2008 | Tomkins et al. |
| D565,735 S | 4/2008 | Washbon |
| 7,359,744 B2 | 4/2008 | Lee et al. |
| 7,383,728 B2 | 6/2008 | Noble et al. |
| 7,391,835 B1 | 6/2008 | Gross et al. |
| 7,408,460 B2 | 8/2008 | Crystal et al. |
| 7,420,464 B2 | 9/2008 | Fitzgerald et al. |
| 7,440,789 B2 | 10/2008 | Hannula et al. |
| 7,443,292 B2 | 10/2008 | Jensen et al. |
| 7,443,693 B2 | 10/2008 | Arnold et al. |
| 7,460,827 B2 | 12/2008 | Schuster et al. |
| 7,463,143 B2 | 12/2008 | Forr et al. |
| 7,463,144 B2 | 12/2008 | Crystal et al. |
| 7,471,978 B2 | 12/2008 | John et al. |
| 7,471,987 B2 | 12/2008 | Crystal et al. |
| 7,483,835 B2 | 1/2009 | Neuhauser et al. |
| 7,496,400 B2 | 2/2009 | Hoskonen et al. |
| 7,548,774 B2 | 6/2009 | Kurtz et al. |
| 7,551,952 B2 | 6/2009 | Gevins et al. |
| 7,592,908 B2 | 9/2009 | Zhang et al. |
| 7,614,066 B2 | 11/2009 | Urdang et al. |
| 7,623,823 B2 | 11/2009 | Zito et al. |
| 7,627,880 B2 | 12/2009 | Itakura |
| 7,636,456 B2 | 12/2009 | Collins et al. |
| 7,650,793 B2 | 1/2010 | Jensen et al. |
| 7,689,272 B2 | 3/2010 | Farwell |
| 7,697,979 B2 | 4/2010 | Martinerie et al. |
| 7,698,238 B2 | 4/2010 | Barletta et al. |
| 7,716,697 B2 | 5/2010 | Morikawa et al. |
| 7,720,351 B2 | 5/2010 | Levitan |
| 7,729,755 B2 | 6/2010 | Laken |
| 7,739,140 B2 | 6/2010 | Vinson et al. |
| 7,742,623 B1 | 6/2010 | Moon et al. |
| 7,751,878 B1 | 7/2010 | Merkle et al. |
| 7,805,009 B2 | 9/2010 | Everett et al. |
| 7,809,420 B2 | 10/2010 | Hannula et al. |
| 7,840,248 B2 | 11/2010 | Fuchs et al. |
| 7,840,250 B2 | 11/2010 | Tucker |
| 7,853,122 B2 | 12/2010 | Miura et al. |
| 7,865,394 B1 | 1/2011 | Calloway |
| 7,892,764 B2 | 2/2011 | Xiong et al. |
| 7,908,133 B2 | 3/2011 | Neuhauser |
| 7,917,366 B1 | 3/2011 | Levanon et al. |
| 7,942,816 B2 | 5/2011 | Satoh et al. |
| 7,946,974 B2 | 5/2011 | Lordereau |
| 7,962,315 B2 | 6/2011 | Jensen et al. |
| 7,988,557 B2 | 8/2011 | Soderland |
| 8,014,847 B2 | 9/2011 | Shastri et al. |
| 8,027,518 B2 | 9/2011 | Baker et al. |
| 8,055,722 B2 | 11/2011 | Hille |
| 8,069,125 B2 | 11/2011 | Jung et al. |
| 8,082,215 B2 | 12/2011 | Jung et al. |
| 8,086,563 B2 | 12/2011 | Jung et al. |
| 8,098,152 B2 | 1/2012 | Zhang et al. |
| 8,103,328 B2 | 1/2012 | Turner et al. |
| 8,112,141 B2 | 2/2012 | Wilson et al. |
| 8,135,606 B2 | 3/2012 | Dupree |
| 8,151,298 B2 | 4/2012 | Begeja et al. |
| 8,165,916 B2 | 4/2012 | Hoffberg et al. |
| 8,179,604 B1 | 5/2012 | Prada Gomez et al. |
| 8,209,224 B2 | 6/2012 | Pradeep et al. |
| 8,229,469 B2 | 7/2012 | Zhang et al. |
| 8,239,030 B1 | 8/2012 | Hagedorn et al. |
| 8,255,267 B2 | 8/2012 | Breiter |
| 8,270,814 B2 | 9/2012 | Pradeep et al. |
| 8,300,526 B2 | 10/2012 | Saito et al. |
| 8,326,396 B2 | 12/2012 | Picht et al. |
| 8,327,395 B2 | 12/2012 | Lee |
| 8,332,883 B2 | 12/2012 | Lee |
| 8,335,715 B2 | 12/2012 | Pradeep et al. |
| 8,386,312 B2 | 2/2013 | Pradeep et al. |
| 8,386,313 B2 | 2/2013 | Pradeep et al. |
| 8,388,165 B2 | 3/2013 | Zhang |
| 8,392,250 B2 | 3/2013 | Pradeep et al. |
| 8,392,251 B2 | 3/2013 | Pradeep et al. |
| 8,392,253 B2 | 3/2013 | Pradeep et al. |
| 8,392,254 B2 | 3/2013 | Pradeep et al. |
| 8,392,255 B2 | 3/2013 | Pradeep et al. |
| 8,396,744 B2 | 3/2013 | Pradeep et al. |
| 8,442,429 B2 | 5/2013 | Hawit |
| 8,467,133 B2 | 6/2013 | Miller |
| 8,473,345 B2 | 6/2013 | Pradeep et al. |
| 8,477,425 B2 | 7/2013 | Border et al. |
| 8,484,081 B2 | 7/2013 | Pradeep et al. |
| 8,494,610 B2 | 7/2013 | Pradeep et al. |
| 8,494,905 B2 | 7/2013 | Pradeep et al. |
| 8,533,042 B2 | 9/2013 | Pradeep et al. |
| 8,548,554 B2 | 10/2013 | Popescu et al. |
| 8,548,852 B2 | 10/2013 | Pradeep et al. |
| 8,635,105 B2 | 1/2014 | Pradeep et al. |
| 8,655,428 B2 | 2/2014 | Pradeep et al. |
| 8,655,437 B2 | 2/2014 | Pradeep et al. |
| 2001/0016874 A1 | 8/2001 | Ono et al. |
| 2001/0020236 A1 | 9/2001 | Cannon |
| 2001/0029468 A1 | 10/2001 | Yamaguchi et al. |
| 2001/0056225 A1 | 12/2001 | DeVito |
| 2002/0065826 A1 | 5/2002 | Bell et al. |
| 2002/0072952 A1 | 6/2002 | Hamzy et al. |
| 2002/0077534 A1 | 6/2002 | DuRousseau |
| 2002/0107454 A1 | 8/2002 | Collura et al. |
| 2002/0143627 A1 | 10/2002 | Barsade et al. |
| 2002/0154833 A1 | 10/2002 | Koch et al. |
| 2002/0155878 A1 | 10/2002 | Lert, Jr. et al. |
| 2002/0156842 A1 | 10/2002 | Signes et al. |
| 2002/0182574 A1 | 12/2002 | Freer |
| 2002/0188216 A1 | 12/2002 | Kayyali et al. |
| 2002/0188217 A1 | 12/2002 | Farwell |
| 2002/0193670 A1 | 12/2002 | Garfield et al. |
| 2003/0003433 A1 | 1/2003 | Carpenter et al. |
| 2003/0013981 A1 | 1/2003 | Gevins et al. |
| 2003/0036955 A1 | 2/2003 | Tanaka et al. |
| 2003/0055355 A1 | 3/2003 | Viertio-Oja |
| 2003/0059750 A1 | 3/2003 | Bindler et al. |
| 2003/0063780 A1 | 4/2003 | Gutta et al. |
| 2003/0066071 A1 | 4/2003 | Gutta et al. |
| 2003/0067486 A1 | 4/2003 | Lee et al. |
| 2003/0073921 A1 | 4/2003 | Sohmer et al. |
| 2003/0076369 A1 | 4/2003 | Resner |

(56) References Cited

U.S. PATENT DOCUMENTS

| | | |
|---|---|---|
| 2003/0081834 A1 | 5/2003 | Philomin et al. |
| 2003/0093784 A1 | 5/2003 | Dimitrova et al. |
| 2003/0100998 A2 | 5/2003 | Brunner et al. |
| 2003/0104865 A1 | 6/2003 | Itkis et al. |
| 2003/0126593 A1 | 7/2003 | Mault |
| 2003/0153841 A1 | 8/2003 | Kilborn |
| 2003/0165270 A1 | 9/2003 | Endrikhovski et al. |
| 2003/0177488 A1 | 9/2003 | Smith et al. |
| 2003/0233278 A1 | 12/2003 | Marshall |
| 2004/0005143 A1 | 1/2004 | Tsuru et al. |
| 2004/0013398 A1 | 1/2004 | Miura et al. |
| 2004/0015608 A1 | 1/2004 | Ellis et al. |
| 2004/0018476 A1 | 1/2004 | Ladue |
| 2004/0039268 A1 | 2/2004 | Barbour et al. |
| 2004/0044382 A1 | 3/2004 | Ibrahim |
| 2004/0072133 A1 | 4/2004 | Kullok et al. |
| 2004/0073129 A1 | 4/2004 | Caldwell et al. |
| 2004/0077934 A1 | 4/2004 | Massad |
| 2004/0088289 A1 | 5/2004 | Xu et al. |
| 2004/0092809 A1 | 5/2004 | DeCharms |
| 2004/0098298 A1 | 5/2004 | Yin |
| 2004/0111033 A1 | 6/2004 | Oung et al. |
| 2004/0122303 A1* | 6/2004 | Kopke ............................ 600/383 |
| 2004/0138546 A1* | 7/2004 | Reho et al. .................... 600/382 |
| 2004/0161730 A1 | 8/2004 | Urman |
| 2004/0187167 A1 | 9/2004 | Maguire et al. |
| 2004/0193068 A1 | 9/2004 | Burton et al. |
| 2004/0208496 A1 | 10/2004 | Pilu |
| 2004/0210159 A1 | 10/2004 | Kibar et al. |
| 2004/0220483 A1 | 11/2004 | Yeo et al. |
| 2004/0236623 A1 | 11/2004 | Gopalakrishnan |
| 2004/0267141 A1 | 12/2004 | Amano et al. |
| 2005/0010087 A1 | 1/2005 | Banet |
| 2005/0010116 A1 | 1/2005 | Korhonen et al. |
| 2005/0010475 A1 | 1/2005 | Perkowski et al. |
| 2005/0043774 A1 | 2/2005 | Devlin et al. |
| 2005/0045189 A1 | 3/2005 | Jay |
| 2005/0066307 A1 | 3/2005 | Patel et al. |
| 2005/0071865 A1 | 3/2005 | Martins |
| 2005/0076359 A1 | 4/2005 | Pierson et al. |
| 2005/0079474 A1 | 4/2005 | Lowe |
| 2005/0096311 A1 | 5/2005 | Suffin et al. |
| 2005/0097594 A1 | 5/2005 | O'Donnell et al. |
| 2005/0107716 A1 | 5/2005 | Eaton et al. |
| 2005/0113656 A1 | 5/2005 | Chance |
| 2005/0120372 A1 | 6/2005 | Itakura |
| 2005/0143629 A1 | 6/2005 | Farwell |
| 2005/0154290 A1 | 7/2005 | Langleben |
| 2005/0165285 A1 | 7/2005 | Iliff |
| 2005/0172311 A1 | 8/2005 | Hjelt et al. |
| 2005/0177058 A1 | 8/2005 | Sobell |
| 2005/0197556 A1 | 9/2005 | Stoler |
| 2005/0197590 A1 | 9/2005 | Osorio et al. |
| 2005/0203798 A1 | 9/2005 | Jensen et al. |
| 2005/0215916 A1 | 9/2005 | Fadem et al. |
| 2005/0223237 A1 | 10/2005 | Barletta et al. |
| 2005/0227233 A1 | 10/2005 | Buxton et al. |
| 2005/0240956 A1 | 10/2005 | Smith et al. |
| 2005/0272017 A1 | 12/2005 | Neuhauser et al. |
| 2005/0273017 A1 | 12/2005 | Gordon |
| 2005/0273802 A1 | 12/2005 | Crystal et al. |
| 2005/0288954 A1 | 12/2005 | McCarthy et al. |
| 2005/0289582 A1 | 12/2005 | Tavares et al. |
| 2006/0003732 A1 | 1/2006 | Neuhauser et al. |
| 2006/0010470 A1 | 1/2006 | Kurosaki et al. |
| 2006/0035707 A1 | 2/2006 | Nguyen et al. |
| 2006/0053110 A1 | 3/2006 | McDonald et al. |
| 2006/0064037 A1 | 3/2006 | Shalon et al. |
| 2006/0093998 A1 | 5/2006 | Vertegaal |
| 2006/0094970 A1 | 5/2006 | Drew |
| 2006/0111044 A1 | 5/2006 | Keller |
| 2006/0111621 A1 | 5/2006 | Coppi et al. |
| 2006/0111644 A1 | 5/2006 | Guttag et al. |
| 2006/0129458 A1 | 6/2006 | Maggio |
| 2006/0143647 A1 | 6/2006 | Bill |
| 2006/0167376 A1 | 7/2006 | Viirre et al. |
| 2006/0168613 A1 | 7/2006 | Wood et al. |
| 2006/0168630 A1 | 7/2006 | Davies |
| 2006/0217598 A1 | 9/2006 | Miyajima et al. |
| 2006/0256133 A1 | 11/2006 | Rosenberg |
| 2006/0257834 A1 | 11/2006 | Lee et al. |
| 2006/0258926 A1 | 11/2006 | Ali et al. |
| 2006/0259360 A1 | 11/2006 | Flinn et al. |
| 2006/0265022 A1 | 11/2006 | John et al. |
| 2006/0277102 A1 | 12/2006 | Agliozzo |
| 2006/0293608 A1 | 12/2006 | Rothman et al. |
| 2006/0293921 A1 | 12/2006 | McCarthy et al. |
| 2007/0031798 A1 | 2/2007 | Gottfried |
| 2007/0048707 A1 | 3/2007 | Caamano et al. |
| 2007/0053513 A1 | 3/2007 | Hoffberg |
| 2007/0055169 A1 | 3/2007 | Lee et al. |
| 2007/0060830 A1 | 3/2007 | Le et al. |
| 2007/0060831 A1 | 3/2007 | Le et al. |
| 2007/0066874 A1 | 3/2007 | Cook |
| 2007/0066914 A1 | 3/2007 | Le et al. |
| 2007/0066915 A1 | 3/2007 | Frei et al. |
| 2007/0066916 A1 | 3/2007 | Lemos |
| 2007/0067007 A1 | 3/2007 | Schulman et al. |
| 2007/0067305 A1 | 3/2007 | Ives |
| 2007/0078706 A1 | 4/2007 | Datta et al. |
| 2007/0079331 A1 | 4/2007 | Datta et al. |
| 2007/0101360 A1 | 5/2007 | Gutta et al. |
| 2007/0106170 A1 | 5/2007 | Dunseath, Jr. et al. |
| 2007/0116037 A1 | 5/2007 | Moore |
| 2007/0135727 A1 | 6/2007 | Virtanen et al. |
| 2007/0135728 A1 | 6/2007 | Snyder et al. |
| 2007/0168461 A1 | 7/2007 | Moore |
| 2007/0173733 A1 | 7/2007 | Le et al. |
| 2007/0179396 A1 | 8/2007 | Le et al. |
| 2007/0184420 A1 | 8/2007 | Mathan et al. |
| 2007/0225585 A1 | 9/2007 | Washbon et al. |
| 2007/0225674 A1 | 9/2007 | Molnar et al. |
| 2007/0226760 A1 | 9/2007 | Neuhauser et al. |
| 2007/0235716 A1 | 10/2007 | Delic et al. |
| 2007/0238945 A1 | 10/2007 | Delic et al. |
| 2007/0249952 A1 | 10/2007 | Rubin et al. |
| 2007/0250846 A1 | 10/2007 | Swix et al. |
| 2007/0255127 A1 | 11/2007 | Mintz et al. |
| 2007/0265507 A1 | 11/2007 | de Lemos |
| 2007/0294132 A1 | 12/2007 | Zhang et al. |
| 2007/0294705 A1 | 12/2007 | Gopalakrishnan |
| 2007/0294706 A1 | 12/2007 | Neuhauser et al. |
| 2008/0001600 A1 | 1/2008 | deCharms |
| 2008/0010110 A1 | 1/2008 | Neuhauser et al. |
| 2008/0027345 A1 | 1/2008 | Kumada et al. |
| 2008/0039737 A1 | 2/2008 | Breiter et al. |
| 2008/0040740 A1 | 2/2008 | Plotnick et al. |
| 2008/0059997 A1 | 3/2008 | Plotnick et al. |
| 2008/0065468 A1 | 3/2008 | Berg et al. |
| 2008/0065721 A1 | 3/2008 | Cragun |
| 2008/0081961 A1 | 4/2008 | Westbrook et al. |
| 2008/0082019 A1 | 4/2008 | Ludving et al. |
| 2008/0086356 A1 | 4/2008 | Glassman et al. |
| 2008/0091512 A1 | 4/2008 | Marci et al. |
| 2008/0097854 A1 | 4/2008 | Young |
| 2008/0109840 A1 | 5/2008 | Walter et al. |
| 2008/0125110 A1 | 5/2008 | Ritter |
| 2008/0127978 A1 | 6/2008 | Rubin et al. |
| 2008/0144882 A1 | 6/2008 | Leinbach et al. |
| 2008/0147488 A1 | 6/2008 | Tunick et al. |
| 2008/0152300 A1 | 6/2008 | Knee et al. |
| 2008/0159365 A1 | 7/2008 | Dubocanin et al. |
| 2008/0162182 A1 | 7/2008 | Cazares et al. |
| 2008/0177197 A1 | 7/2008 | Lee et al. |
| 2008/0201731 A1 | 8/2008 | Howcraft |
| 2008/0204273 A1 | 8/2008 | Crystal et al. |
| 2008/0208072 A1 | 8/2008 | Fadem et al. |
| 2008/0211768 A1 | 9/2008 | Breen et al. |
| 2008/0214902 A1 | 9/2008 | Lee et al. |
| 2008/0218472 A1 | 9/2008 | Breen et al. |
| 2008/0221400 A1 | 9/2008 | Lee et al. |
| 2008/0221472 A1 | 9/2008 | Lee et al. |
| 2008/0221969 A1 | 9/2008 | Lee et al. |
| 2008/0222670 A1 | 9/2008 | Lee et al. |

(56) References Cited

U.S. PATENT DOCUMENTS

| | | |
|---|---|---|
| 2008/0222671 A1 | 9/2008 | Lee et al. |
| 2008/0228077 A1 | 9/2008 | Wilk et al. |
| 2008/0255949 A1 | 10/2008 | Genco et al. |
| 2008/0295126 A1 | 11/2008 | Lee et al. |
| 2008/0306398 A1 | 12/2008 | Uchiyama et al. |
| 2008/0312523 A1 | 12/2008 | Dunseath |
| 2009/0024049 A1 | 1/2009 | Pradeep et al. |
| 2009/0024447 A1 | 1/2009 | Pradeep et al. |
| 2009/0024448 A1 | 1/2009 | Pradeep et al. |
| 2009/0024449 A1 | 1/2009 | Pradeep et al. |
| 2009/0024475 A1 | 1/2009 | Pradeep et al. |
| 2009/0025023 A1 | 1/2009 | Pradeep et al. |
| 2009/0025024 A1 | 1/2009 | Beser et al. |
| 2009/0030287 A1 | 1/2009 | Pradeep et al. |
| 2009/0030303 A1 | 1/2009 | Pradeep et al. |
| 2009/0030717 A1 | 1/2009 | Pradeep et al. |
| 2009/0030762 A1 | 1/2009 | Lee et al. |
| 2009/0030930 A1 | 1/2009 | Pradeep et al. |
| 2009/0036755 A1 | 2/2009 | Pradeep et al. |
| 2009/0036756 A1 | 2/2009 | Pradeep et al. |
| 2009/0037575 A1 | 2/2009 | Crystal et al. |
| 2009/0060240 A1 | 3/2009 | Coughlan et al. |
| 2009/0062629 A1 | 3/2009 | Pradeep et al. |
| 2009/0062679 A1 | 3/2009 | Tan et al. |
| 2009/0062680 A1 | 3/2009 | Sandford |
| 2009/0062681 A1 | 3/2009 | Pradeep et al. |
| 2009/0063255 A1 | 3/2009 | Pradeep et al. |
| 2009/0063256 A1 | 3/2009 | Pradeep et al. |
| 2009/0069652 A1 | 3/2009 | Lee et al. |
| 2009/0070798 A1 | 3/2009 | Lee et al. |
| 2009/0082643 A1 | 3/2009 | Pradeep et al. |
| 2009/0082689 A1 | 3/2009 | Guttag et al. |
| 2009/0083129 A1 | 3/2009 | Pradeep et al. |
| 2009/0088610 A1 | 4/2009 | Lee et al. |
| 2009/0089830 A1 | 4/2009 | Chandratillake et al. |
| 2009/0094286 A1 | 4/2009 | Lee et al. |
| 2009/0094627 A1 | 4/2009 | Lee et al. |
| 2009/0094628 A1 | 4/2009 | Lee et al. |
| 2009/0094629 A1 | 4/2009 | Lee et al. |
| 2009/0097689 A1 | 4/2009 | Prest et al. |
| 2009/0105576 A1 | 4/2009 | Do et al. |
| 2009/0112077 A1 | 4/2009 | Nguyen et al. |
| 2009/0119154 A1 | 5/2009 | Jung et al. |
| 2009/0131764 A1 | 5/2009 | Lee et al. |
| 2009/0133047 A1 | 5/2009 | Lee et al. |
| 2009/0150919 A1 | 6/2009 | Lee et al. |
| 2009/0156925 A1 | 6/2009 | Jin et al. |
| 2009/0158308 A1 | 6/2009 | Weitzenfeld et al. |
| 2009/0163777 A1 | 6/2009 | Jung |
| 2009/0195392 A1 | 8/2009 | Zalewski |
| 2009/0214060 A1 | 8/2009 | Chuang et al. |
| 2009/0222330 A1 | 9/2009 | Leinbach |
| 2009/0248484 A1 | 10/2009 | Surendran et al. |
| 2009/0248496 A1 | 10/2009 | Hueter et al. |
| 2009/0253996 A1 | 10/2009 | Lee et al. |
| 2009/0259137 A1 | 10/2009 | Delic et al. |
| 2009/0271122 A1 | 10/2009 | Hyde et al. |
| 2009/0292587 A1 | 11/2009 | Fitzgerald |
| 2009/0318773 A1 | 12/2009 | Jung et al. |
| 2009/0318826 A1 | 12/2009 | Green et al. |
| 2009/0327068 A1 | 12/2009 | Pradeep et al. |
| 2009/0328089 A1 | 12/2009 | Pradeep et al. |
| 2010/0004977 A1 | 1/2010 | Marci et al. |
| 2010/0022821 A1 | 1/2010 | Dubi et al. |
| 2010/0041962 A1 | 2/2010 | Causevic et al. |
| 2010/0042012 A1 | 2/2010 | Alhussiny |
| 2010/0060300 A1 | 3/2010 | Muller et al. |
| 2010/0075532 A1 | 3/2010 | Copp-Howland et al. |
| 2010/0076333 A9 | 3/2010 | Burton et al. |
| 2010/0081902 A1* | 4/2010 | McKenna et al. ............ 600/324 |
| 2010/0125190 A1 | 5/2010 | Fadem |
| 2010/0125219 A1 | 5/2010 | Harris et al. |
| 2010/0145176 A1 | 6/2010 | Himes |
| 2010/0145215 A1 | 6/2010 | Pradeep et al. |
| 2010/0145217 A1 | 6/2010 | Otto et al. |
| 2010/0180029 A1 | 7/2010 | Fourman |
| 2010/0183279 A1 | 7/2010 | Pradeep et al. |
| 2010/0186031 A1 | 7/2010 | Pradeep et al. |
| 2010/0186032 A1 | 7/2010 | Pradeep et al. |
| 2010/0198042 A1 | 8/2010 | Popescu et al. |
| 2010/0214318 A1 | 8/2010 | Pradeep et al. |
| 2010/0215289 A1 | 8/2010 | Pradeep et al. |
| 2010/0218208 A1 | 8/2010 | Holden |
| 2010/0249538 A1 | 9/2010 | Pradeep et al. |
| 2010/0249636 A1 | 9/2010 | Pradeep et al. |
| 2010/0250325 A1 | 9/2010 | Pradeep et al. |
| 2010/0250458 A1 | 9/2010 | Ho |
| 2010/0257052 A1 | 10/2010 | Zito et al. |
| 2010/0268540 A1 | 10/2010 | Arshi et al. |
| 2010/0268573 A1 | 10/2010 | Jain et al. |
| 2010/0269127 A1 | 10/2010 | Krug |
| 2010/0274152 A1 | 10/2010 | McPeck et al. |
| 2010/0274153 A1 | 10/2010 | Tucker et al. |
| 2010/0306120 A1 | 12/2010 | Ciptawilangga |
| 2010/0317988 A1 | 12/2010 | Terada et al. |
| 2010/0325660 A1 | 12/2010 | Holden |
| 2010/0331661 A1 | 12/2010 | Nakagawa |
| 2011/0004089 A1 | 1/2011 | Chou |
| 2011/0015503 A1 | 1/2011 | Joffe et al. |
| 2011/0040202 A1 | 2/2011 | Luo et al. |
| 2011/0046473 A1 | 2/2011 | Pradeep et al. |
| 2011/0046502 A1 | 2/2011 | Pradeep et al. |
| 2011/0046503 A1 | 2/2011 | Pradeep et al. |
| 2011/0046504 A1 | 2/2011 | Pradeep et al. |
| 2011/0047121 A1 | 2/2011 | Pradeep et al. |
| 2011/0059422 A1 | 3/2011 | Masaoka |
| 2011/0085700 A1 | 4/2011 | Lee |
| 2011/0098593 A1 | 4/2011 | Low et al. |
| 2011/0105937 A1 | 5/2011 | Pradeep et al. |
| 2011/0106621 A1 | 5/2011 | Pradeep et al. |
| 2011/0106750 A1 | 5/2011 | Pradeep et al. |
| 2011/0119124 A1 | 5/2011 | Pradeep et al. |
| 2011/0119129 A1 | 5/2011 | Pradeep et al. |
| 2011/0131274 A1 | 6/2011 | Hille |
| 2011/0144519 A1 | 6/2011 | Causevic |
| 2011/0151728 A1 | 6/2011 | Astola |
| 2011/0153391 A1 | 6/2011 | Tenbrock |
| 2011/0161163 A1 | 6/2011 | Carlson et al. |
| 2011/0161790 A1 | 6/2011 | Junior et al. |
| 2011/0191142 A1 | 8/2011 | Huang |
| 2011/0208515 A1 | 8/2011 | Neuhauser |
| 2011/0224569 A1 | 9/2011 | Isenhart et al. |
| 2011/0237923 A1 | 9/2011 | Picht et al. |
| 2011/0237971 A1 | 9/2011 | Pradeep et al. |
| 2011/0248729 A2 | 10/2011 | Mueller et al. |
| 2011/0257502 A1 | 10/2011 | Lee |
| 2011/0257937 A1 | 10/2011 | Lee |
| 2011/0270620 A1 | 11/2011 | Pradeep et al. |
| 2011/0276504 A1 | 11/2011 | Pradeep et al. |
| 2011/0282231 A1 | 11/2011 | Pradeep et al. |
| 2011/0282232 A1 | 11/2011 | Pradeep et al. |
| 2011/0282749 A1 | 11/2011 | Pradeep et al. |
| 2011/0298706 A1 | 12/2011 | Mann |
| 2011/0301431 A1 | 12/2011 | Greicius |
| 2011/0319975 A1 | 12/2011 | Ho et al. |
| 2012/0003862 A1 | 1/2012 | Newman et al. |
| 2012/0004899 A1 | 1/2012 | Arshi |
| 2012/0022391 A1 | 1/2012 | Leuthardt |
| 2012/0036004 A1 | 2/2012 | Pradeep et al. |
| 2012/0036005 A1 | 2/2012 | Pradeep et al. |
| 2012/0054018 A1 | 3/2012 | Pradeep et al. |
| 2012/0072289 A1 | 3/2012 | Pradeep et al. |
| 2012/0096363 A1 | 4/2012 | Barnes et al. |
| 2012/0108995 A1 | 5/2012 | Pradeep et al. |
| 2012/0114305 A1 | 5/2012 | Holden |
| 2012/0130800 A1 | 5/2012 | Pradeep et al. |
| 2012/0173701 A1 | 7/2012 | Tenbrock |
| 2012/0190959 A1* | 7/2012 | Hayakawa et al. ............ 600/383 |
| 2012/0197144 A1 | 8/2012 | Christ et al. |
| 2012/0203363 A1 | 8/2012 | McKenna et al. |
| 2012/0203559 A1 | 8/2012 | McKenna et al. |
| 2012/0239407 A1 | 9/2012 | Jain et al. |
| 2012/0245978 A1 | 9/2012 | Crystal et al. |
| 2012/0249797 A1 | 10/2012 | Haddick et al. |

(56) References Cited

U.S. PATENT DOCUMENTS

| | | | | |
|---|---|---|---|---|
| 2012/0253159 | A1* | 10/2012 | Medina et al. | 600/340 |
| 2013/0024272 | A1 | 1/2013 | Pradeep et al. | |
| 2013/0060125 | A1 | 3/2013 | Zeman | |
| 2013/0166373 | A1 | 6/2013 | Pradeep et al. | |
| 2013/0185140 | A1 | 7/2013 | Pradeep et al. | |
| 2013/0185141 | A1 | 7/2013 | Pradeep et al. | |
| 2013/0185142 | A1 | 7/2013 | Pradeep et al. | |
| 2013/0185144 | A1 | 7/2013 | Pradeep et al. | |
| 2013/0185145 | A1 | 7/2013 | Pradeep et al. | |
| 2013/0311132 | A1 | 11/2013 | Tobita | |
| 2013/0332259 | A1 | 12/2013 | Pradeep et al. | |
| 2014/0213881 | A1* | 7/2014 | Banet et al. | 600/393 |

FOREIGN PATENT DOCUMENTS

| | | |
|---|---|---|
| EP | 1052582 | 11/2000 |
| EP | 1389012 | 2/2004 |
| EP | 1607842 | 12/2005 |
| FR | 2627975 | 9/1989 |
| GB | 1374658 | 11/1974 |
| GB | 2221759 | 2/1990 |
| JP | 02-243131 | 9/1990 |
| JP | 05-293172 | 11/1993 |
| JP | 07-329657 | 12/1995 |
| JP | 10-2000-0072489 | 12/2000 |
| JP | 2002-000577 | 1/2002 |
| JP | 2002-056500 | 2/2002 |
| JP | 2002-344904 | 11/2002 |
| JP | 2003-016095 | 1/2003 |
| JP | 2003-111106 | 4/2003 |
| JP | 2003-178078 | 6/2003 |
| JP | 2003-522580 | 7/2003 |
| JP | 2005-160805 | 12/2003 |
| JP | 2004-527843 | 9/2004 |
| JP | 2005261076 | 9/2005 |
| JP | 2005-084770 | 3/2006 |
| JP | 2006-305334 | 3/2006 |
| JP | 2006-323547 | 11/2006 |
| JP | 2011-104338 | 6/2011 |
| KR | 10-2001-0104579 | 11/2001 |
| KR | 20120129870 | 11/2012 |
| WO | 95-18565 | 7/1995 |
| WO | 97-17774 | 5/1997 |
| WO | 97-40745 | 11/1997 |
| WO | 97-41673 | 11/1997 |
| WO | 00/17824 | 3/2000 |
| WO | 01/97070 | 12/2001 |
| WO | 02-084624 | 10/2002 |
| WO | 02-100241 | 12/2002 |
| WO | 02-102238 | 12/2002 |
| WO | 2004-049225 | 6/2004 |
| WO | 2004/100765 | 11/2004 |
| WO | 2006/005767 | 1/2006 |
| WO | 2007/019584 | 2/2007 |
| WO | 2008-077178 | 7/2008 |
| WO | 2008-109694 | 9/2008 |
| WO | 2008-109699 | 9/2008 |
| WO | 2008-121651 | 10/2008 |
| WO | 2008-141340 | 10/2008 |
| WO | 2008-137579 | 11/2008 |
| WO | 2008-137581 | 11/2008 |
| WO | 2008-154410 | 12/2008 |
| WO | 2009-018374 | 2/2009 |
| WO | 2009-052833 | 4/2009 |
| WO | 2011-055291 | 5/2011 |
| WO | 2011-056679 | 5/2011 |

OTHER PUBLICATIONS

International Search Report and Written Opinion, issued by the International Searching Authority in connection with corresponding International patent application No. PCT/US2014/020255, mailed on May 23, 2014, 15 pages.

Aaker et al., "Warmth in Advertising: Measurement, Impact, and Sequence Effects," Journal of Consumer Research, vol. 12, No. 4, pp. 365-381, Mar. 1986, 18 pages.

Adamic et al., "The political blogosphere and the 2004 U.S. election: Divided they blog," Proceedings WWW-2005 2nd Annual Workshop on the Weblogging Ecosystem, 2005, Chiba, Japan, 16 pages.

Adar et al., "Implicit structure and the dynamics of blogspace," Proceedings WWW-2004 Workshop on the Weblogging Ecosystem, 2004, New York, NY, 8 pages.

Akam, et al., "Oscillations and Filtering Networks Support Flexible Routing of Information," Neuron, vol. 67, pp. 308-320, Elsevier, Jul. 29, 2010, 13 pages.

Aliod et al., "A Real World Implementation of Answer Extraction," Department of Computer Science, University of Zurich, Winterthurerstr. 190, CH-8057 Zurich, Switzerland, 1998, 6 pages.

Allen et al., "A Method of Removing Imaging Artifact from Continuous EEG Recorded during Functional MRI," Neuroimage, vol. 12, 230-239, Aug. 2000, 12 pages.

Ambler, "Salience and Choice: Neural Correlates of Shopping Decisions," Psychology & Marketing, vol. 21, No. 4, p. 247-261, Wiley Periodicals, Inc., doi: 10.1002/mar20004, Apr. 2004, 16 pages.

Ambler et al., "Ads on the Brain; A Neuro-Imaging Comparison of Cognitive and Affective Advertising Stimuli," London Business School, Centre for Marketing Working Paper, No. 00-902, Mar. 2000, 23 pages.

Badre, et al. "Frontal Cortex and the Discovery of Abstract Action Rules," Neuron, vol. 66, pp. 315-326, Elsevier, Apr. 29, 2010, 12 pages.

Bagozzi et al., "The Role of Emotions in Marketing," Journal of the Academy of Marketing Science, vol. 27, No. 2, pp. 184-206, Academy of Marketing Science, 1999, 23 pages.

Barcelo, et al., "Prefrontal modulation of visual processing in humans," Nature Neuroscience, vol. 3, No. 4, Nature America, http://neurosci.nature.com, Apr. 2000, 5 pages.

Barreto et al., "Physiologic Instrumentation for Real-time Monitoring of Affective State of Computer Users," WSEAS International Conference on Instrumentation, Measurement, Control, Circuits and Systems (IMCCAS), 2004, 6 pages.

Beaver, John D., et al., "Individual Differences in Reward Drive Predict Neural Responses to Images of Food", J. of Neuroscience, (May 10, 2006), 5160-5166, 7 pages.

Belch et al., "Psychophysiological and cognitive Response to Sex in Advertising," Advances in Consumer Research, vol. 9, pp. 424-427, 1982, 6 pages.

Bimler et al., "Categorical perception of facial expressions of emotion: Evidence from multidimensional scaling," Cognition and Emotion, vol. 15(5), pp. 633-658 Sep. 2001, 26 pages.

Bishop, Mike, "ARROW Question/Answering Systems," Language Computer Corporation, 1999, 3 pages.

Bizrate, archived version of www.bizrate.com, Jan. 1999, 22 pages.

Blakeslee, "If You Have a 'Buy Button' in Your Brain, What Pushes It?" The New York Times, www.nytimes.com, Oct. 19, 2004, 3 pages.

Blum, "Empirical Support for Winnow and Weighted-Majority Algorithms: Results on a Calendar Scheduling Domain," in Machine Learning, vol. 26, Kluwer Academic Publishers, Boston, USA, 1997, 19 pages.

Bournellis, Cynthia, "Tracking the hits on Web Sites," Communications International: vol. 22, Issue 9, London, Sep. 1995, 3 pages.

Braeutigam, "Neuroeconomics-From neural systems to economic behavior," Brain Research Bulletin, vol. 67, pp. 355-360, Elsevier, 2005, 6 pages.

Buschman, et al., "Top-Down versus Bottom-Up Control of Attention in the Prefrontal and posterior Parietal Cortices," Science, vol. 315, www.sciencemag.org/cgi/content/full/315/5820/1860, American Association for the Advancement of Science, 2007, 4 pages.

Buschman, et al., "Serial, Covert Shifts of Attention during Visual Search Are Reflected by the Frontal Eye Fields and Correlated with Population Oscillations," Neuron, vol. 63, pp. 386-396, Elsevier, Aug. 13, 2009, 11 pages.

Canolty, et al., "High Gamma Power Is Phase-Locked to Theta Oscillations in Human Neocortex," Science, vol. 313, www.sciencemag.org, Sep. 15, 2006, 3 pages.

(56) References Cited

OTHER PUBLICATIONS

Chaum et al., "A Secure and Privacy-Protecting Protocol for Transmitting Personal Information Between Organizations," A.M. Odlyzko (Ed.): Advances in Cryptology, CRYPTO '86, LNCS 263, 1987, 51 pages.
Chaum, David L., "Untraceable Electronic Mail, Return Addresses and Digital Pseudonyms," Communication of the ACM, vol. 24, No. 2, 1981, 5 pages.
Carter, R., "Mapping the Mind," 1998, University of California Press, Berkeley, 3 pages.
Cheng, et al. "Gender Differences in the Mu Rhythm of the Human Minor-Neuron System," PLos ONE, vol. 3, Issue 5, www.plosone.org, May 2008, 7 pages.
Clarke, Adam R. et al., "EEG Analysis of Children with Attention-Deficit/Hyperactivity Disorder and Comorbid Reading Disabilities," Journal of Learning Disabilities, vol. 35, No. 3, May-Jun. 2002, 10 pages.
Clemons, "Resonance Marketing in the Age of the Truly Informed Consumer: Creating Profits through Differentiation and Delight," Wharton Information Strategy & Economics Blog 2, available at http://opim.wharton.upenn.edu/~clemons/blogs/resonanceblog.pdf, Mar. 28, 2007, 8 pages.
Clifford, "Billboards That Look Back," The New York Times, NYTimes.com, available at http://www.nytimes.com/2008/05/31/business/media/31billboard.html, May 31, 2008, 4 pages.
Coan et al., "Voluntary Facial Expression and Hemispheric Asymmetry Over the Frontal Cortex," Psycophysiology (Nov. 2001), 912-924, 14 pages.
Cohen, William W., "Data Integration using similarity joins and a word-based information representation language," ACM Transactions on Information Systems, vol. 18, No. 3, Jul. 2000, 34 pages.
Cohn et al., "Active Learning with Statistical Models," Journal of Artificial Intelligence Research 4, AI Access Foundation and Morgan Kaufmann Publishers, USA, 1996, 17 pages.
Crawford et al., "Self-generated happy and sad emotions in low and highly hypnotizable persons during waking and hypnosis: laterality and regional EEG activity differences," International Journal of Psychophysiology, vol. 24, pp. 239-266, Dec. 1996, 28 pages.
Dagan et al., "Mistake-Driven Learning in Text Categorization," in EMNLP '97, $2^{nd}$ Conference on Empirical Methods in Natural Language Processing, 1997, 9 pages.
Davidson, et al., "The functional neuroanatomy of emotion and affective style," TRENDS in Cognitive Sciences, vol. 3, No. 1, Jan. 1999, 11 pages.
de Gelder et al., "Categorical Perception of Facial Expressions: Categories and their Internal Structure," Cognition and Emotion, vol. 11(1), pp. 1-23 1997, 23 pages.
D'Esposito, "From cognitive to neural models of working memory," Phil. Trans. R. Soc. B, doi: 10.1098/rstb.2007.2086, Mar. 30, 2007, 12 pages.
Delahaye group, "Delahaye Group to Offer Nets Bench: High Level Web-Site Qualitative Analysis and Reporting; NetBench Builds on Systems provided by I/PRO and Internet Media Services," 1995 Business Wire, Inc., May 31, 1995, 3 pages.
Desmet, "Measuring Emotion: Development and Application of an Instrument to Measure Emotional Responses to Products," to be published in Funology: From Usability to Enjoyment, pp. 111-123, Kluwer Academic Publishers, (Blythe et al., eds., 2004), 13 pages.
Dialogic, www.dialogic.com as archived on May 12, 2000, 34 pages.
Dien, et al., "Application of Repeated Measures ANOVA to High-Dens Dataset: A Review and Tutorial," in Event-Related Potentials: A Methods Handbook pp. 57-82, (Todd C. Handy, ed., 2005), 14 pages.
Dillon et al., "Marketing research in a Marketing Environment," Times Mirror/Mosby College, USA, 1987, 5 pages.
Duchowski, "A Breadth-First Survey of Eye-tracking Applications," Beahavior Research Methods, Instruments, and Computers (Nov. 2002), 455-470, 16 pages.
Edgar, et al., "Digital Filters in ERP Research," in Event-Related Potentials: A Methods Handbook pp. 85-113, (Todd C. Handy, ed., 2005), 15 pages.

EEG Protocols, "Protocols for EEG Recording," retrieved from the Internet on Aug. 23, 2011, http://www.q-metrx.com/EEGrecordingProtocols.pdf, Nov. 13, 2007, 3 pages.
Egner et al., "EEG Signature and Phenomenology of Alpha/theta Neurofeedback Training Versus Mock Feedback," Applied Psychophysiology and Biofeedback, vol. 27, No. 4, Dec. 2002, 10 pages.
El-Bab, M., "Congnative event related potentials during a learning task," Doctoral Dissertation, Faculty of Medicine, University of Southamption, 2001, 25 pages.
Engel et al., "Dynamic Predictions: Oscillations and Synchrony in Top-down Processing," Nature Reviews: Neuroscience, vol. 2, pp. 704-716, Macmillian Magazines Ltd., Oct. 2001, 13 pages.
Ewatch, eWatch's archived web site retrieved from [URL: http://web.archive.org/web/19980522190526/wwww.ewatch.com] on Sep. 8, 2004, archived May 22, 1998, 50 pages.
Farber, Dave, "IP: eWatch and Cybersleuth," retrieved from [URL: http://www.interesting-people.org/archives/interesting-people/200006/msg00090.html] Jun. 29, 2000, 4 pages.
Filler, "MR Neurography and Diffusion Tensor Imaging: Origins, History & Clinical Impact of the first 50,000 Cases With an Assortment of Efficacy and Utility in a Prospective 5,000 Patent Study Group," Institute for Nerve Medicine, Nov. 7, 2008, 56 pages.
Flinker, A. et al, "Sub-centimeter language organization in the human temporal lobe," Brain and Language, Elsevier Inc., (2010), doi.org/10.1016/j.bandl.2010.09.009, 7 pages.
Fogelson, et al., "Prefrontal cortex is critical for contextual processing: evidence from brain lesions," Brain: A Journal of Neurology, vol. 132, pp. 3002-3010, doi:10.1093/brain/awp230, Aug. 27, 2009, 9 pages.
Freund et al., "Selective Sampling Using the Query by Committee Algorithm," Machine Learning 28 Kluwer Academic Publishers, The Netherlands, 1997, 36 pages.
Friedman, et al., "Event-Related Potential (ERP) Studies of Memory Encoding and Retrieval: A Selective Review," Microscopy Research and Technique 51:6-26, Wiley-Less, Inc., 2000, 23 pages.
Fries, "A mechanism for cognitive dynamics: neuronal coherence," Trends in Cognitive Sciences, vol. 9, No. 10, pp. 474-480, Elsevier B.V. www.sciencedirect.com, Oct. 2005, 7 pages.
Fuster, "Cortex and Memory: Emergence of a New Paradigm," Journal of Cognitive Neuroscience, vol. 21, No. 11, pp. 2047-2072, Massachusetts Institute of Technology, Nov. 2009, 26 pages.
Gaillard, "Problems and Paradigms in ERP Research," Biological Psychology, Elsevier Science Publisher B.V., 1988, 10 pages.
Gargiulo et al., "A Mobile EEG System With Dry Electrodes," (Nov. 2008), 4 pages.
Gazzaley et al., "Top-down Enhancement and Suppression of Magnitude and Speed of Neural Activity," Journal of Cognitive Neuroscience, vol. 17, No. 3, pp. 507-517, Massachusetts Institute of Technology, 2005, 11 pages.
Gevins et al., "High resolution EEG mapping of cortical activation related to a working memory," Cereb Cprtex. 7, 1997, 12 pages.
Glance et al., "Analyzing online disussion for marketing intelligence," Proceedings WWW-2005 2nd Annual Workshop on the Weblogging Ecosystem, Chiba, Japan, 2005, 2 pages.
Glance et al., "Deriving marketing intelligence from online discussion," 11th ACM SIGKDD International Conference on Knowledge Discovery and Data Mining, Chicago, IL, Aug 21-24, 2005, 10 pages.
Grefensette et al., "Validating the Coverage of Lexical Resources for Affect Analysis and Automatically Classifying New Words along Semantic Axes," Chapter X, Mar. 3, 2004, 16 pages.
Griss et al., "Characterization of micromachined spiked biopotential electrodes", Biomedical Engineering, IEEE Transactions Jun. 2002, 8 pages.
Haq, "This Is Your Brain on Advertising," BusinessWeek, Market Research, Oct. 8, 2007, 3 pages.
Harabagiu, Sanda M., "An Intelligent System for Question Answering," University of Southern California; Modlovan, Dan, Southern Methodist University, 1996, 5 pages.
Harabagiu, Sanda M., "Experiments with Open-Domain Textual Question Answering," Department of Computer Science and Engineering at Southern Methodist Universtity, 2000, 7 pages.

(56) References Cited

OTHER PUBLICATIONS

Harabagiu, Sanda M., "Mining Textual Answers with Knowledge-Based Indicators," Department of Computer Science and Engineering at Southern Methodist University, 2000, 5 pages.
Harland, C.J. et al., "Remote detection of human electroencephalograms using ultrahigh input impedance electrical potential sensors," Applied Physics Letters., vol. 81, No. 17, Oct. 21, 2002, 3 pages.
Harmony et al., "Specific EEG frequencies signal general common congnative processes as well as specific tasks processes in man," International Journal of Psycophysiology, 53, 2004, 10 pages.
Hartikainen et al., Manuscript Draft of "Emotionally arousing stimuli compete with attention to left hemispace," NeuroReport, Sep. 8, 2007, 26 pages.
Hazlett, et al., "Emotional Response to Television Commercials: Facial EMG vs. Self-Report," Journal of Advertising Research, Apr. 1999, 17 pages.
Heo et al., "Wait! Why is it Not Moving? Attractive and Distractive Ocular Responses to Web Ads," Paper presented to AEJMC, (Aug. 2001) Washington, DC, available at http://www.psu.edu/dept/medialab/researchpage/newabstracts/wait.html, 3 pages.
Herrmann, et al., "Mechanisms of human attention: event-related potentials and oscillations," Neuroscience and Biobehavioral Reviews, pp. 465-476, Elsevier Science Ltd., www.elsevier.com/locate/neubiorev, 2001, 12 pages.
Hopf, et al., "Neural Sources of Focused Attention in Visual Search," Cerebral Cortex, 10:1233-1241, Oxford University Press, Dec. 2000, 9 pages.
Housley et al., "Internet X.509 Public Key Infrastructure Certificate and CRL Profile," Network Working Group Request for Comments: 2459, Jan. 1999, 121 pages.
Hughes, et al., "Conventional and Quantatative Electroencephalography in Psychiatry," Journal of Neuropsychiatry and Clinical Neurosciences, vol. 11(2), 1999, 19 pages.
Joachims, Thorsten, "Text Categorization with Support Vector Machines: Learning with Many Relevant Features," in Machine Learning: ECML-98, Tenth European Conference on Machine Learning, 1998, 7 pages.
Jung et al., "Analysis and Visualization of Single-Trial Event-Related Potentials," Human Brain Mapping vol. 14, 166-185 2001, 20 pages.
Kahn et al., "Categorizing Web Documents using Competitive Learning: An ingredient of a Personal Adaptive Agent," IEEE 1997, 4 pages.
Katz, Boris, "From Sentence Processing to Information Access on the World Wide Web," MIT Artificial Intelligence Laboratory, Feb. 27, 1997, 20 pages.
Kay et al., "Identifying natural images from human brain activity," Nature, vol. 452, pp. 352-356, Nature Publishing Group, Mar. 20, 2008, 5 pages.
Keren, et al., "Saccadic spike potentials in gamma-band EEG: Characterization, detection and suppression," NeuroImage, http://dx.doi:10.10161j.neuroimage.2009.10.057, Oct. 2009, 16 pages.
Kishiyama, et al., "Novelty Enhancements in Memory Are Dependent on Lateral Prefrontal Cortex," The Journal of Neuroscience, pp. 8114-8118, Society for Neuroscience Jun. 24, 2009, 5 pages.
Kishiyama, et al., "Socioeconomic Disparities Affect Prefrontal Function in Children," Journal of Cognitive Neuroscience pp. 1106-1115, Massachusetts Institute of Technology, 2008, 10 pages.
Kleppner, "Advertising Procedure," 6th edition, 1977, Prentice-Hall, Inc., Englewood Cliffs, NJ, p. 492, 3 pages.
Klimesch, "EEG alpha and theta oscillations reflect cognitive and memory performance a review and analysis," Brain Research Reviews, vol. 29, 169-195, 1999, 27 pages.
Klimesch, et al. "Episodic and semantic memory: an analysis in the EEG theta and alpha band," Electroencephalography Clinical Neurophysiology, 1994, 14 pages.
Kotler, "Marketing Management," PrenticeHall International Inc., Upper Saddle River, NJ, 1997, 10 pages.
Knight, "Contribution of human hippocampal region to novelty detection," Nature, vol. 383, www.nature.com, Sep. 19, 1996, 4 pages.
Knight, "Consciousness Unchained: Ethical Issues and the Vegetative and minimally Conscious State," The American Journal of Bioethics, 8:9, 1-2, http://dx.doi.org/10.1080/15265160802414524, Sep. 1, 2008), 3 pages.
Knight, et al., "Prefrontal cortex regulates inhibition and excitation in distributed neural networks," Acta Psychologica vol. 101, pp. 159-178, Elsevier 1999, 20 pages.
Knight, "Decreased Response to Novel Stimuli after Prefrontal Lesions in Man," Electroencephalography and Clinical Neurophysiology, vol. 59, pp. 9-20, Elsevier Scientific Publishers Ireland, Ltd., 1984, 12 pages.
Krakow et al., "Methodology: EEG-correlated fMRI," Functional Imaging in the Epilepsies, Lippincott Williams & Wilkins, 2000, 17 pages.
Krugman, "Brain Wave Measures of Media Involvement," Journal of Advertising Research vol. 11, Feb. 3-9, 1971, 7 pages.
Lachaux et al., "Measuring Phase Synchrony in Brain Signals," Human Brain Mapping 8, 1999, 194-208, 15 pages.
Lee et al., "What is 'neuromarketing'? A discussion and agenda for future research," International Journal of Psychophysiology, vol. 63, pp. 199-204, Elsevier 2006, 6 pages.
Lekakos, "Personalized Advertising Services Through Hybrid Recommendation Methods: The Case of Digital Interactive Television," Department of Informatics, Cyprus University, 2004, 11 pages.
Lenz et al., "Question answering with Textual CBR," Department of Computer Science, Humboldt University Berlin, D-10099 Berlin, 1998, 12 pages.
Lewis et al., "Market Researchers make Increasing use of Brain Imaging," ACNR, vol. 5, No. 3, pp. 36-37, Jul./Aug. 2005, 2 pages.
Littlestone, Nick, "Learning Quickly When Irrelevant Attributes Abound: A New Linear-threshold Algorithm," in Machine Learning, vol. 2, Kluwer Academic Publishers, Boston, MA, 1988, 34 pages.
Luck, et al., "The speed of visual attention in schizophrenia: Electrophysiological and behavioral evidence," Schizophrenia Research, pp. 174-195, Elsevier B.V. www.sciencedirect.com, 2006, 22 pages.
Lui et al., "Marketing Strategies in Virtual Worlds," The Data Base for Advances in Information Systems, vol. 38, No. 4, pp. 77-80, Nov. 2007, 4 pages.
Makeig, et al., "Mining event-related brain dynamics," Trends in Cognitive Sciences, vol. 8, No. 5, May 2004, www.sciencedirect.com, 7 pages.
Makeig, et al., "Dynamic Brain Sources of Visual Evoked Responses," Science, vol. 295, www.sciencemag.org, Jan. 25, 2002, 5 pages.
Marlow, "Audience, structure and authority in the weblog community," International Communication Association Conference, MIT Media Laboratory, New Orleans, LA 2004, 9 pages.
The Mathworks, Inc., "MATLAB Data Analysis: Version 7," p. 4-19 2005, 3 pages.
McCallum et al., "Text Classification by Bootstrapping with the Keywords, EM and Shrinkage," Just Research and Carnegie Mellon University, Pittsburgh, PA, circa 1999, 7 pages.
McLachlan et al., "The EM Algorithm and Extensions," John Wiley & Sons, Inc., New York, NY, 1997, 302 pages.
Meriam-Webster Online Dictionary definition for "tangible," available at http://www.meriam-webster.com/dictionary/tangible, 1 page.
Meriam Webster Online Dictionary, Definition of Virtual Reality, available at http://www.meriam-webster.com/dictionary/virtual%20reality, 2 page.
Miltner, et al., "Coherence of gamma-band EEG activity as a basis for associative learning," Nature, vol. 397, www.nature.com, Feb. 4, 1999, 3 pages.
Mizuhara et al., A long range cortical network emerging with theta oscillation in mental task, Neuroreport 15 (8), 2004, 11 pages.
Moldovan et al., "LASSO: A Tool for Surfing the Answer Net," Department of Computer Science and Engineering at Southern Methodist University, 1999, 9 pages.
Mosby's Dictionary of Medicine, Nursing, & Health Professions, 2009, Mosby, Inc., Definition of Alpha Wave, 1 page.

(56) References Cited

OTHER PUBLICATIONS

Mosby's Dictionary of Medicine, Nursing, & Health Professions, 2009, Mosby, Inc., Definition of Beta Wave, 1 page.
Nakashima et al., "Information Filtering for the Newspaper," IEEE 1997, 4 pages.
Nanno et al., "Automatic collection and monitoring of Japanese Weblogs," Proceedings WWW-2004 Workshop on the weblogging Ecosystem, 2004, New York, NY, 7 pages.
Netcurrent, NetCurrent's web site, http://web.archive.org/web/20000622024845/www.netcurrents.com, retrieved on Jan. 17, 2005, archived on Jun. 22, 2000 and Sep. 18, 2000, 17 pages.
Neurofocus—Neuroscientific Analysis for Audience Engagement, accessed on Jan. 8, 2010 at http://web.archive.org/web/20080621114525/www.neurofocus.com /BrandImage.htm, 2008, 2 pages.
Newell et al., "Categorical perception of familiar objects," Cognition, vol. 85, Issue 2, pp. 113-143 Sep. 2002, 31 pages.
Nielsen, "Neuroinformatics in Functional Neuroimaging," Informatics and Mathematical Modeling, Technical University of Denmark, Aug. 30, 2002, 241 pages.
Oberman et al., "EEG evidence for mirror neuron activity during the observation of human and robot actions Aug. 29, 2012 Toward an analysis of the human qualities of interactive robots," Neurocomputing 70, 2007 2194-2203, 10 pages.
Osborne, "Embedded Watermarking for image Verification in Telemedicine," Thesis submitted for the degree of Doctor of Philosophy, Electrical and Electronic Engineering, University of Adelaide, 2005, 219 pages.
Padgett et al., "Categorical Perception in Facial Emotion Classification," In Proceedings of the 18th Annual Conference of the Cognitive Science Society, pp. 249-253, 1996, 5 pages.
Page et al., "Cognitive Neuroscience, Marketing and Research," Congress 2006—Foresight—The Predictive Power of Research Conference Papers, ESOMAR Publications, Sep. 17, 2006, 25 pages.
Paller, et al., "Validating neural correlates of familiarity," TRENDS in Cognitive Sciences, vol. 11, No. 6, www.sciencedirect.com, May 2, 2007, 8 pages.
Palva et al., "Phase Synchrony Among Neuronal Oscillations in the Human Cortex," Journal of Neuroscience 25 2005, 3962-3972, 11 pages.
Pang et al., "Thumbs up? Sentiment Classification using Machine Learning Techniques," in Proceedings of EMNLP 2002, 8 pages.
Picton, et al., "Guidelines for using human event-related potentials to study cognition: Recording standards and publication criteria," Psychophysiology, pp. 127-152, Society for Psychophysiological Research, 2000, 26 pages.
Reguly, "Caveat Emptor Rules on the Internet," The Globe and Mail (Canada): Report on Business Column, Apr. 10, 1999, 2 pages.
Reinartz, "Customer Lifetime Value Analysis: An Integrated Empirical Framework for Measurement and Explanation," dissertation, University of Houston, Faculty of College of Business Administration, Apr. 1999, 68 pages.
Rizzolatti et al., "The Mirror-Neuron System," Annu. Rev. Neurosci., vol. 27, pp. 169-192, Mar. 5, 2004, 30 pages.
Rothschild et al., "Predicting Memory for Components of TV Commercials from EEG," Journal of Consumer Research (Mar. 1990), p. 472-478, 8 pages.
Ruchkin et al., "Modality-specific processing streams in verbal working memory: evidence from spatio-temporal patterns of brain activity," Cognitive Brain Research, vol. 6, pp. 95-113, Elsevier, 1997, 19 pages.
Rugg, et al., "Event-related potentials and recognition memory," TRENDS in Cognitive Sciences, vol. 11, No. 6, www.sciencedirect.com, May 3, 2007, 7 pages.
Rugg, et al., "The ERP and cognitive psychology: conceptual issues," Sep. 1996, 7 pages.
"User monitoring," Sapien Systems, available at http://web.archive.org/web/20030818043339/http:/www.sapiensystems.com/eyetracking.html, Aug. 18, 2003, 1 pages.
Sammler, "Music and emotion: Electrophysiological correlates of the processing of pleasant and unpleasant music," Psychophysiology, vol. 44, Blackwell Publishing Inc., 2007, 12 pages.
Schmidt et al., "Frontal brain electrical activity (EEG) distinguishes valence and intensity of musical emotions," Cognition and Emotion, vol. 15 (4), Psychology Press Ltd, 2001, 14 pages.
Selden, G., "Machines that Read Minds," Science Digest, Oct. 1981, 9 pages.
Shandlen, Michael N. et al., "A Computational Analysis of the Relationship between Neuronal and Behavioral Responses to Visual Motion", The Journal of Neuroscience, (Feb. 15, 1996) 1486-1510, 25 pages.
Simon-Thomas, et al, "Behavioral and Electrophysiological Evidence of a Right Hemisphere Bias for the Influence of Negative Emotion on Higher Cognition," Journal of Cognitive Neuroscience, pp. 518-529, Massachusetts Institute of Technology 2005, 12 pages.
Soderland et al., "Customer Satisfaction and Links to Customer Profitability: An Empirical Examination of the Association Between Attitudes and Behavior," SSE/EFI Working Paper Series in Business Administration, Jan. 1999, 22 pages.
Spencer, "Averaging, Detection, and Classification of Single-Trial ERPs," in Event-Related Potentials: A Methods Handbook, pp. 209-227, (Todd C. Handy, ed., 2005), 10 pages.
Arousal in Sport, in Encyclopedia of Applied Psychology, vol. 1, p. 159, retrieved from Google Books, (Spielberger, ed., Elsevier Academic Press, 2004), 1 page.
Srinivasan, "High-Resolution EEG: Theory and Practice," in Event-Related Potentials: A Methods Handbook, pp. 167-188, (Todd C. Handy, ed., 2005), 12 pages.
Sullivan et al., "A brain-machine interface using dry-contact, low-noise EEG sensors," In Proceedings of the 2008 IEEE International Symposium on Circuits and Systems, May 18, 2008, 4 pages.
Sutherland, "Neuromarketing: What's it all about?" Retrieved from Max Sutherland's Weblog on Aug. 23, 2011, http://www.sutherlandsurvey.com/Column_pages/Neuromarketing_whats_it_all_about.htm, Mar. 2007, 5 pages.
Swick, et al., "Contributions of Prefrontal Cortex to Recognition Memory: Electrophysiological and Behavioral Evidence," Neuropsychology, vol. 13, No. 2, pp. 155-170, American Psychological Association, Inc. 1999, 16 pages.
Taheri, et al., "A dry electrode for EEG recording," Electroencephalography and clinical Neurophysiology, pp. 376-383, Elsevier Science Ireland Ltd., 1994, 8 pages.
Talsma, et al., "Methods for the Estimation and Removal of Artifacts and Overlap in ERP Waveforms," in Event-Related Potentials: A Methods Handbook, pp. 115-148, (Todd C. Handy, ed., 2005), 22 pages.
Tapert, Susan F., et al., "Neural Response to Alcohol Stimuli in Adolescents With Alcohol Use Disorder", Arch Gen Psychiatry (Jul. 2003), 727-735, 9 pages.
"Technology Platform: SmartShirt + Eye-Tracking," Innerscope Research, Mar. 2007, 1 page.
Thomas, "International Marketing," International Textbook Company, Scranton, PA 1971, 3 pages.
Trigaux, Robert, "Cyberwar Erupts Over Free Speech Across Florida, Nation," Knight-Ridder Tribune Business News, May 29, 2000, 4 pages.
Tull et al., "Marketing Research Measurement and Method," MacMillan Publishing Company, New York, NY, 1984, 9 pages.
Vogel, et al., "Electrophysiological Evidence for a Postperceptual Locus of Suppression During the Attentional Blink," Journal of Experimental Psychology: Human Perception and Performance, vol. 24, No. 6, pp. 1656-1674, 1998, 19 pages.
Voorhees, Ellen M., "The TREC-8 Question Answering Track Report," National Institute of Standards and Technology, 1999, 6 pages.
Voytek, et al., "Prefrontal cortex and basal ganglia contributions to visual working memory," PNAS Early Edition, www.pnas.org/cgi/doi/10.1073/pnas.1007277107, 2010, 6 pages.
Voytek, et al., "Hemicraniectomy: A New Model for Human Electrophysiology with High Spatio-temporal Resolution," Journal of Cognitive Neuroscience, vol. 22, No. 11, pp. 2491-2502, Massachusetts Institute of Technology, Nov. 2009, 12 pages.

(56) References Cited

OTHER PUBLICATIONS

Wang, "Neurophysiological and Computational Principles of Cortical Rhythms in Cognition," Physiol Rev 90: pp. 1195-1268, American Physiological Society, www.prv.org, (2010), 75 pages.
Wiebe et al., "Identifying Collocations for Recognizing Opinions," in proceedings of ACL/EACL '01 Workshop on Collocation, Toulouse, France, Apr. 9, 2001, 9 pages.
Willis et al., "Discover Your Child's Learning Style: Children Learn in Unique Ways—Here's the Key to Every Child's Learning Success," Prime Publishing, 1999, 22 pages.
Anonymous, "Functional magnetic resonance imaging," retrieved online from Wikipedia, the Free Encyclopedia on Aug. 23, 2011, at http://en.wikipedia.org/w/index.php?title=Functional_magnetic_resonance_imaging&oldid=319601772, Oct. 13, 2009, 8 pages.
William, "Brain Signals to Control Movement of Computer Cursor," Blog article: Brain Signals to Control Movement of Computer Cursor, Artificial Intelligence, retrieved from the Internet on Aug. 17, 2011, http://whatisartificialintelligence.com/899/brain-signals-to-control-movement-of-computer-cursor/, Feb. 17, 2010, 3 pages.
Wise, A., "The High Performance Mind, Mastering Brainwaves for Insight, Healing and Creativity," G.P. Putnam's Son, New York, 1996, pp. 13-15; 20-22; 143-156, 11 pages.
Wise, A., "The High Performance Mind, Mastering Brainwaves for Insight, Healing and Creativity," G.P. Putnam's Son, New York, 1996, pp. 156-158; 165-170; 186-187, 15 pages.
Woldorf, "Distortion of ERP averages due to overlap from temporally adjacent ERPs: Analysis and correction," Psychophysiology, Society for Psychophysiological Research, Cambridge University Press, 1993, 22 pages.
Woodman, et al., "Serial Deployment of Attention During Visual Search," Journal of Experimental Psychology: Human Perception and Performance, vol. 29, No. 1, pp. 121-138, American Physiological Association(2003, 18 pages.
Word of Mouth Research Case Study, "The Trans Fat Issue, Analysis of online consumer conversation to understand how the Oreo lawsuit impacted word-of-mouth on trans fats," Aug. 16, 2004, 35 pages.
Yamaguchi, et al., "Rapid-Prefrontal—Hippocampal Habituation to Novel Events," The Journal of Neuroscience, pp. 5356-5363, Society for Neuroscience, (Apr. 29, 2004), 8 pages.
Yang, "An Evaluation of Statistical Approaches to Text Categorization," Information Retrieval 1 (1/2) Apr. 10, 1999, 12 pages.
Yap et al., "TIMER: Tensor Image Morphing for Elastic Registration," NeuroImage, vol. 47, May 3, 2009, 15 pages.

Yuval-Greenberg, et al., "Transient Induced Gamma-Bands Response in EEG as a Manifestation of Miniature Saccades," Neuron, vol. 58, pp. 429-441, Elsevier Inc. May 8, 2008, 13 pages.
Zagat, www.zagat.com, archived on Apr. 29, 1999, 33 pages.
Zagat, www.zagat.com, archived version of p. 34, Feb. 1999, 1 page.
Zhang, P., "Will You Use Animation on Your Web Pages?" Doing Business on the Internet: Opportunities and Pitfalls, C. Romm and F. Sudweeks (eds.), Spring-Verlag, 1999, 17 pages.
Ziegenfuss, "Neuromarketing: Advertising Ethical & Medical Technology," The Brownstone Journal, vol. XII, Boston University, pp. 69-73, May 2005, 5 pages.
Zyga, "A Baseball Cap That Can Read Your Mind," PhysOrg.com, located at www.physorg.com/news130152277.html, May 16, 2008, 11 pages.
Merriam-Webster Online Dictionary, Definition for "Resonance," available at http://www.merriam-webster.com/dictionary/resonance, 4 pages.
Enghoff, Sigurd, Thesis: "Moving ICA and Time-Frequency Analysis in Event-Related EEG Studies of Selective Attention," Technical University of Denmark, Dec. 1999, 54 pages.
Robertson, Adi, "Sony imagines 'Smart Wig' to monitor health, give directions and read facial expressions," http://www.theverge.com/2013/11/21/5129554/bizarre-sony-smartwig-patent-turns-wigs-into-wearable-computing-device, Nov. 21, 2013, 2 pages.
Meriam-Webster Online Dictionary definition for "tangible," retrieved from [URL http://www.meriam-webster.com/dictionary/tangible] on Jan. 1, 2012, 1 page.
Meriam Webster Online Dictionary, Definition of Virtual Reality, retrieved from [URL: http://www.meriam-webster.com/dictionary/virtual%20reality] on Feb. 25, 2012, 2 pages.
Merriam-Webster Online Dictionary, Definition for "Resonance," retrieved from [URL: http://www.merriam-webster.com/dictionary/resonance] on Apr. 10, 2013, 4 pages.
International Preliminary Report on Patentability and Written Opinion, issued by the International Searching Authority in connection with International patent application No. PCT/US2014/020255, mailed on Sep. 24, 2015, 12 pages.
Notification of the First Office Action, issued by the State Intellectual Property Office of the P.R. China, in connection 'with Chinese Patent Application No. 201480001432.2, on Dec. 4, 2015, 14 pages.
Search Report, issued by the State Intellectual Property Office of the P.R. China, in connection with Chinese Patent Application No. 201480001432.2, on Nov. 25, 2015, 4 pages.
Notification of Reason(s) for Rejection, issued by the Japanese Intellectual Property Office in connection with Japanese Patent Application No. JP2015-524516, on Jan. 5, 2016, 10 pages.

* cited by examiner

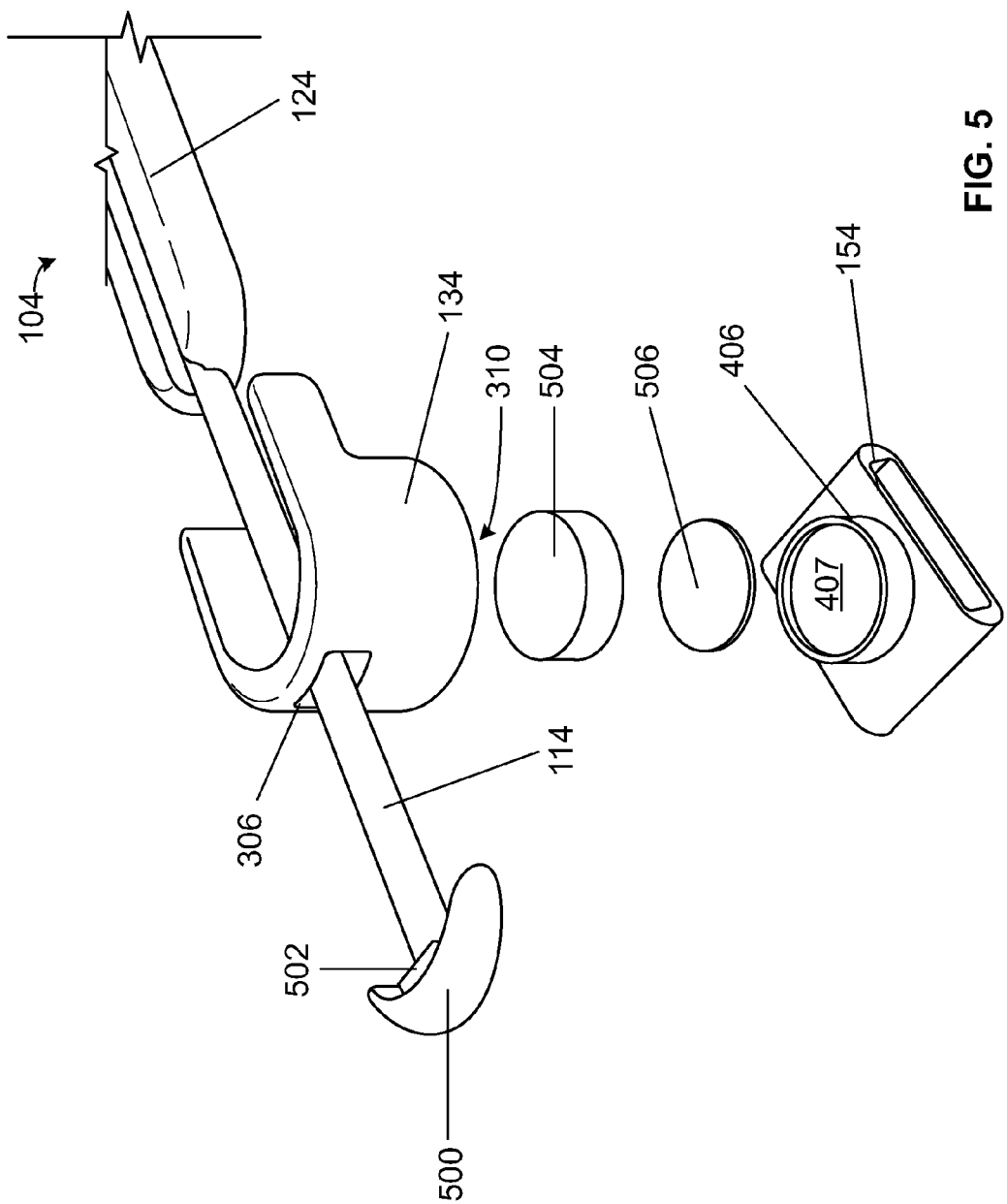

METHODS AND APPARATUS TO GATHER AND ANALYZE ELECTROENCEPHALOGRAPHIC DATA

FIELD OF THE DISCLOSURE

This disclosure relates generally to neurological and physiological monitoring, and, more particularly, to methods and apparatus to gather and analyze electroencephalographic data.

BACKGROUND

Electroencephalography (EEG) involves measuring and recording electrical activity resulting from thousands of simultaneous neural processes associated with different portions of the brain. EEG data is typically measured using a plurality of electrodes placed on the scalp of a person to measure voltage fluctuations resulting from this electrical activity within the neurons of the brain. Subcranial EEG can measure electrical activity with high accuracy. Although bone and dermal layers of a human head tend to weaken transmission of a wide range of frequencies, surface EEG also provides useful electrophysiological information.

BRIEF DESCRIPTION OF THE DRAWINGS

FIG. 5 is an exploded view of the example fastener of FIG. 2.

DETAILED DESCRIPTION

Figure 1A:
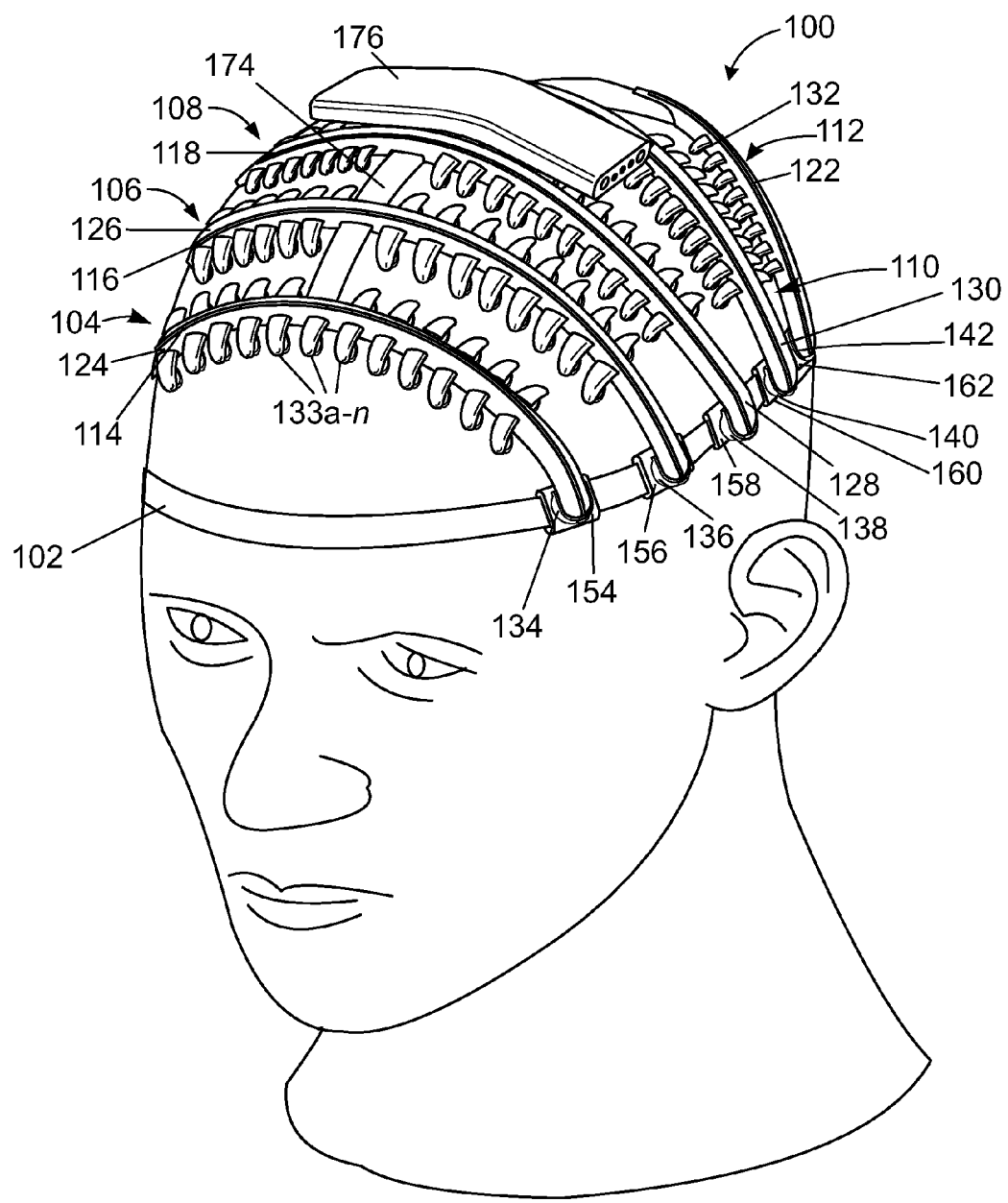
FIG. 1A illustrates a perspective view of an example headset with example removable strips for gathering EEG signals in accordance with the teaching of this disclosure.

Certain examples are shown in the above-identified figures and disclosed in detail below. In describing these examples, like or identical reference numbers are used to identify the same or similar elements. The figures are not necessarily to scale and certain features and certain views of the figures may be shown exaggerated in scale or in schematic for clarity and/or conciseness. Additionally, several examples have been described throughout this specification.

Biological cells and tissues have electrical properties that can be measured to provide information regarding the functioning of the cell or tissue. Various types of electrophysiological techniques have been developed to measure electrical signals from a body. For example, electrocardiography (ECG or EKG) measures electrical activity in a heart. Electroencephalography (EEG) measures electrical activity in a brain. Electrocorticography (ECoG) measures electrical activity using electrodes placed directly on an exposed surface of a brain to record electrical activity in a cerebral cortex. Electromyography (EMG) measures electrical activity in a muscle. Electrooculography (EOG) measures the resting potential of a retina, and electroretinography measures electrical responses of retinal cells. These and/or other electrophysiological signals are important in the treatment, diagnosis and monitoring of many health conditions.

EEG data is indicative of electrical activity of neurons including neural depolarization in the brain due to stimuli of one or more of the five senses (evoked activity) as well as from thought processes (spontaneous activity) that generate electrical activity in the brain. Summations of these electrical activities, (e.g., brainwaves), propagate to the surface (e.g., the scalp) and are detectable with electroencephalograms. Current flow in the human body is due to ion flow. Thus, a biopotential electrode is used to form an electrical double layer with the human skin to sense the ion distribution.

EEG data can be classified in various bands. Brainwave frequencies include delta, theta, alpha, beta and gamma frequency ranges. Delta waves are classified as those less than about 4 Hertz (Hz) and are prominent during sleep. Theta waves have frequencies between about 3.5 Hz to about 7.5 Hz and are associated with memories, attention, emotions, and sensations. Theta waves are typically prominent during states of internal focus. Alpha frequencies reside between about 7.5 Hz and about 13 Hz. Alpha waves are prominent during states of relaxation. Beta waves have a frequency range between about 14 Hz and about 30 Hz. Beta waves are prominent during states of motor control, long range synchronization between areas, analytical problem solving, judgment, and decision making. Gamma waves occur between about 30 Hz and about 100 Hz and are involved in binding of different populations of neurons together into a network for the purpose of carrying out a certain cognitive or motor function, as well as in attention and memory. Skull and dermal layers tend to attenuate waves above about 75 Hz and, as a result, high gamma band or kappa band waves are less easily measured than waves in lower frequency bands. EEG data may be used to determine an emotional or mental state of a person including, for example, attention, emotional engagement, memory or resonance, etc.

EEG signals may be measured using a plurality of electrodes placed on a scalp of a person (e.g., a user, a viewer, a subject, a panelist, a participant or a patient) to measure voltage fluctuations lasting milliseconds and resulting from electrical activity associated with post synaptic currents occurring within neurons of a brain. Though subcranial EEG can measure electrical activity with high accuracy, surface electrodes such as, for example, dry electrodes also provide useful neuro-response information.

To enable the surface EEG electrodes to effectively receive signals from the brain, the electrodes are placed as close to the scalp as possible. The electrodes may be manually placed upon a subject's head or may be contained in a wearable apparatus such as, for example, a headset. Many known EEG headsets utilize a bulky helmet or complicated head-strap type assembly. To decrease impedance, these headsets are typically strapped tightly onto a user's head to decrease the distance between the electrodes and the tissue of the scalp. However, too much pressure such as, for example, greater than two Newtons per millimeter square ($N/mm^2$) results in discomfort for the subject. Further, these known headsets have limited adjustability and are often uncomfortable to wear because they do not account for differently sized heads and/or shapes of heads.

Example headset devices and accompanying components for receiving neuro-response data from a person's brain are disclosed herein. An example headset disclosed herein is portable and comprises a plurality of independently adjustable strips attached to a headband. In some examples, the strips are removable. The examples headset devices into which electrodes are incorporated are adjustable to enhance comfort and noise reduction, as disclosed in greater detail below. Some such example headsets provide a simple, cost effective and reliable solution for the use of a large number of dry electrodes. Some such example headsets ensure comfort, good electrode contact, through the hair operation, and shielding against line noise and other type(s) of noise. Examples disclosed herein also include independently removable and adjustable components to enhance comfort, wearability and safety.

Example clips are also disclosed herein that retain electrodes such as, for example, ground or reference electrodes. In some examples, the clips are used to attach one or more electrodes directly to the body of a person, and the clips are self-fastening such as, for example, with magnetic fasteners, so that additional hardware is not needed to secure the electrodes to the body such as, for example, to an earlobe of the person. Example clips also include terminals to releasably couple the clips and, thus, the electrodes, to a processing unit coupled to the headset. The terminals may also use magnetic fasteners. These example ground electrodes enhance the safety of the headset. For example, if a person were to fall or otherwise cause the headset to become off-balance, the releasable fasteners of the clip and the terminal can disengage from the ear of the person and/or from the processing unit.

An example apparatus is disclosed herein that includes a band to be worn on a head of a person and a first strip adjustably coupled to the band. The example apparatus also includes a first set of electrodes coupled to the first strip to gather a first set of signals from the head and a magnetic fastener to couple the first strip to the band.

In some examples, the apparatus includes a support and the first strip coupled to the support. In some such examples, the apparatus also includes a second strip having a second set of electrodes and the second strip is adjustably coupled to the band and coupled to the support. In some examples, the first strip and the second strip are independently adjustable. In some examples, the first strip and/or the second strip is slidably coupled to the support. In some examples, the first strip and the second strip are independently slidable relative to the support.

In some examples, the apparatus includes a processing unit and the first set of electrodes is communicatively coupled to the processing unit. In some such examples, the apparatus also includes a first reference electrode communicatively coupled to the processing unit. In some examples, the first reference electrode is coupled to a first terminal having a first connector and the first terminal is couplable to the processing unit. In some examples, the first connector comprises a magnetic connector. In some examples, the first connector comprises a first pin and the processing unit comprises a first aperture to receive the first pin. In some examples, the apparatus also includes a second reference electrode communicatively coupled to the processing unit and the second reference electrode is coupled to a second terminal having a second connector the second terminal is coupled to at least one of the processing unit or the first terminal. In some such examples, the second connector comprises a magnetic connector. In some examples, the first connector comprises a first pin and the processing unit comprises a first aperture to receive the first pin, and the second connector comprises a second pin and the first connector comprises a second aperture to receive the second pin.

In some examples, the magnetic fastener comprises a first housing coupled to the band, a second housing coupled to the first strip, and a second magnetic element coupled to the second housing, the second magnetic element to magnetically couple to the first magnetic element. In some such examples, the first housing comprises the first magnetic element. In some examples, the first housing comprises an aperture to receive the band. In some examples, the first housing is adjustably coupled to the band. In some examples, the first housing comprises a protrusion to engage the band. In some such examples, the protrusion comprises a leaf spring.

In some examples, one of the first magnetic element or the second element comprises a metal plate and the other of the first magnetic element or the second magnetic element comprises a magnet. In some examples, the first strip is adjustably coupled to the second housing.

Also disclosed herein are example methods that include adjusting a first strip relative to a band worn on a head of a person using a magnetic fastener and gathering a first set of signals from the head using a first set of electrodes coupled to the first strip.

In some examples, the method includes sliding the first strip relative to a support coupled to the band. In some such examples, the method includes adjusting a second strip relative to the band and gathering a second set of signals from the head using a second set of electrodes coupled to the second strip. In some such examples, the method includes independently adjusting the first strip and the second strip relative to the band. In some examples, the method includes independently adjusting the first strip and the second strip relative to the support.

In some examples, the first set of electrodes is communicatively coupled to a processing unit. In some examples, the method includes communicatively coupling a first reference electrode to the processing unit. In some such examples, the method also includes coupling a first connector of a first terminal to which the first reference electrode is coupled to the processing unit to communicatively couple the first reference electrode and the processing unit. In some examples, the method includes magnetically coupling the first connector of the first terminal to the processing unit. In some examples, the first connector comprises a first pin and the processing unit comprises a first aperture to receive the first pin. In some examples, the method includes coupling a second connector of a second terminal to which a second reference electrode is coupled to at least one of the processing unit or the first terminal to communicatively couple the second reference electrode to the processing unit. In some examples, the method includes magnetically coupling the second connector to at least one of the processing unit or the first terminal. In some examples, the first connector comprises a first pin and the processing unit comprises a first aperture to receive the first pin, and the second connector comprises a second pin and the first connector comprises a second aperture to receive the second pin.

In some examples, the adjusting comprises changing an effective length of the first strip and engaging a first magnetic element coupled to the band with a second magnetic element coupled to the first strip. In some such examples, the first magnetic element is disposed in a first housing. In some examples, the first housing comprises an aperture to receive the band. In some such examples, the method includes adjusting the first housing in which magnetic element is disposed relative to the band. In some examples, the method includes securing the first housing in a position relative to the band. In some examples, the method includes engaging the band with a protrusion of the first housing to secure the first housing in the position. In some such examples, the protrusion comprises a leaf spring.

In some examples, one of the first magnetic element or the second magnetic element comprises a metal plate and the other of the first magnetic element or the second magnetic element comprises a magnet.

In some examples, the method includes adjusting the first strip relative to a second housing in which the second magnetic element is disposed.

An example apparatus disclosed herein includes a housing having a first end, a second end and an intermediary portion. The example apparatus also includes a first cavity adjacent the first end, a second cavity adjacent the second end, a first electrode disposed in the first cavity and a first magnetic element disposed in the second cavity.

In some examples, the first magnetic element is magnetically couplable to a band to dispose the first electrode against a forehead of a subject.

In some examples, the intermediary portion is elastically bendable to oppose the first cavity and the second cavity. In some such examples, the apparatus is couplable to an ear of a subject. In some examples, a magnetic force of the first magnetic element is to secure the apparatus to an ear of a person. In some examples, the first magnetic element is to magnetically couple the first end and the second end. In some examples, the apparatus includes a second magnetic element in the first cavity and the first magnetic element is magnetically couplable to the second magnetic element.

In some examples, the first electrode is coupled to a first terminal. In some such examples, the first terminal is magnetically couplable to a processing unit. In some examples, the processing unit is disposed on a head of a person.

In some examples, the apparatus includes a second electrode disposed in the second cavity. In some such examples, the first electrode is coupled to a first terminal, the second electrode is coupled to a second terminal and the second terminal is removably coupled to the first terminal. In some examples, the second terminal is magnetically coupled to the first terminal.

In some examples, the intermediary portion comprises a plurality of slits to hold a wire, which couples the first electrode to a first terminal.

An example method disclosed herein includes coupling, to a head of a person, a device comprising a housing having a first end, a second end and an intermediary portion. The device also comprises a first cavity adjacent the first end, a second cavity adjacent the second end, a first electrode disposed in the first cavity, and a first magnetic element disposed in the second cavity. The example method also includes gathering a reference signal from the first electrode.

In some examples, the example method includes magnetically coupling the first magnetic element to a band to be worn on the head of the person to dispose the first electrode against a forehead of the person.

In some examples, the method includes elastically bending the intermediary portion to oppose the first cavity and the second cavity. In some such examples, the method includes coupling the device to an ear of the person. In some examples, the method includes magnetically securing the device to the ear of the person by using magnetic force of the first magnetic element. In some examples, the method includes magnetically coupling the first magnetic element to the first end. In some examples, the method includes magnetically coupling the first magnetic element to a second magnetic element disposed in the first cavity.

In some examples, the method includes coupling the first electrode to a first terminal. In some such examples, the method includes magnetically coupling the first terminal to a processing unit. In some examples the method includes disposing the processing unit on a head of the person.

In some examples, the method includes disposing a second electrode in the second cavity. In some such examples, the method includes coupling the first electrode to a first terminal, coupling the second electrode to a second terminal and removably coupling the second terminal to the first terminal. In some examples, the method includes magnetically coupling the second terminal to the first terminal.

In some examples, the method includes weaving a wire through a plurality of slits in the intermediary portion, where the wire couples the first electrode to a first terminal.

Figure 1B:
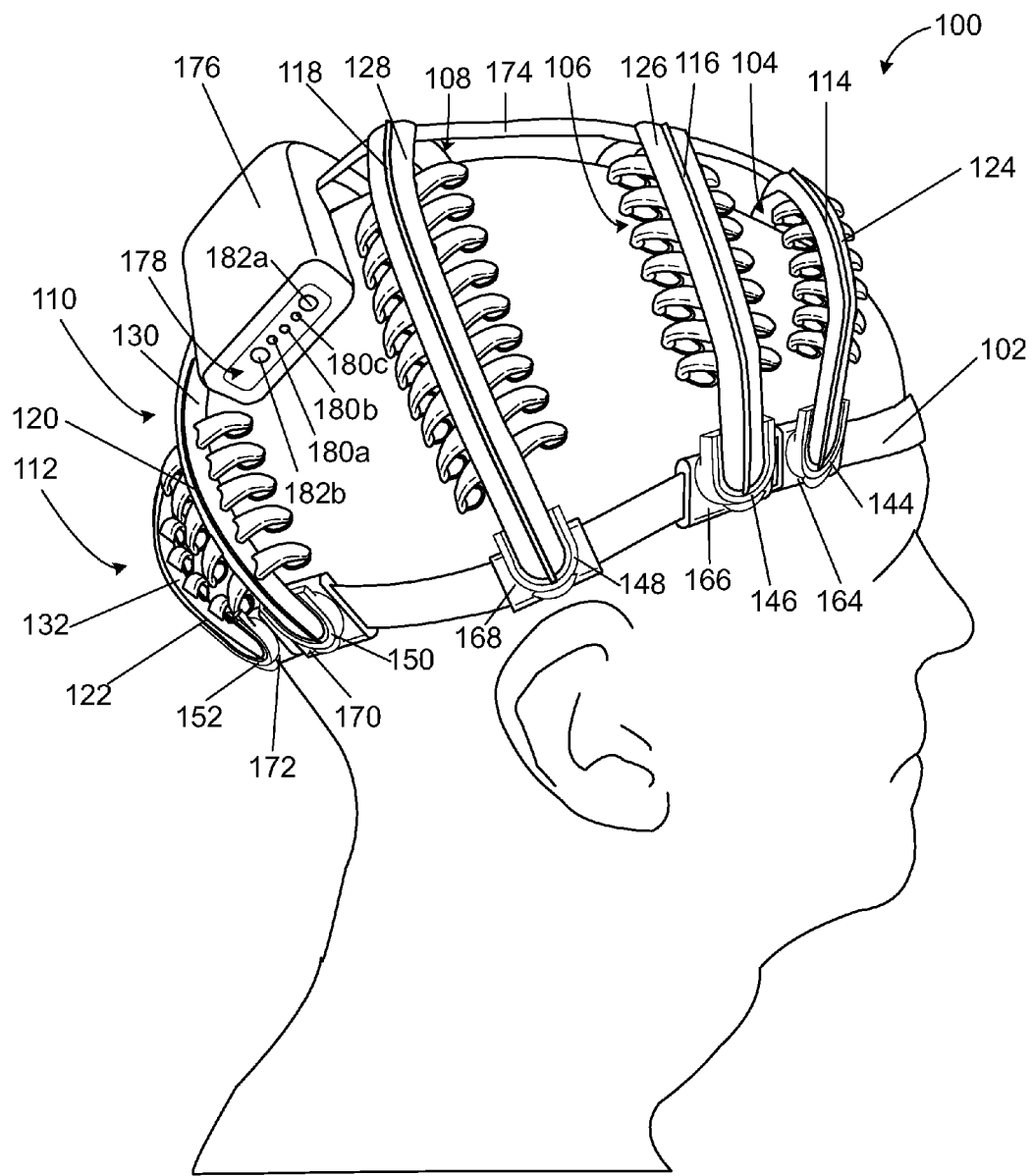
FIG. 1B illustrates a side view of the example headset with the example removable strips shown in FIG. 1A.

Turning now to the figures, FIGS. 1A and 1B show an example headset 100 for gathering EEG signals via the scalp of a person. FIG. 1A illustrates a perspective view of the front and left side of the person's head, and FIG. 1B illustrates a right side view of the person's head. The example headset 100 may be used for instance, to gather medical information from a patient in a medical or a home environment, to control aspects of a game or other entertainment device, to provide data as part of a fitness regime, to collect audience measurement data, to control remote devices and/or multiple other uses. The example headset of FIGS. 1A and 1B includes a band 102 (e.g., a headband, an elastic band, a strap), which may be continuous or include multiple adjustably connected portions, and which is to be worn around a head of a person, a user, a subject, a viewer, a participant and/or panelist.

As used herein, a participant is a person who has agreed to be monitored. Typically, a participant provides his or her demographic information (e.g., age, race, income, etc.) to a monitoring entity (e.g., The Nielsen Company) that collects and compiles data about a topic of interest (e.g., media exposure).

The example headset 100 includes a plurality of strips, each strip having a plurality of electrodes for receiving signals from the head of the person along the respective strip. More specifically, the headset 100 of the illustrated example includes a first strip 104, a second strip 106, a third strip 108, a fourth strip 110 and a fifth strip 112. Each of the strips 104-112 is intended to be worn over the head of a person from the left side of the head to the right side of the head. Each of the example strips 104-112 is removably attached to the band 102 and each of the strips 104-112 is adjustable on the band 102 to move and position the strips 104-112 in specific locations on the head of a person for reading electrical activity via the scalp. In other examples, the headset 100 may include fewer or more strips (e.g., four or less strips, ten or more strips).

As shown in FIGS. 1A and 1B, each of the example strips 104-112 includes a respective strap 114-122 and a respective spine structure 124-132. In some examples, the straps 114-122 are stretchable and may be made of, for example, elastic. As shown, each of the strips 104-112 includes a plurality (e.g., an array) of individual electrodes 133a-n. In the example shown, the electrodes of each strip 104-112 are integrated into the respective spine structures 124-132 along with other electrical components such as, for example, a printed circuit board ("PCB"). A description of example spine structures can be found in U.S. patent application Ser. No. 13/728,900, titled "SYSTEMS AND METHODS TO GATHER AND ANALYZE ELECTROENCEPHALO-GRAPHIC DATA," filed on Dec. 27, 2012, U.S. patent application Ser. No. 13/728,913 titled "SYSTEMS AND METHODS TO GATHER AND ANALYZE ELECTROENCEPHALOGRAPHIC DATA," filed on Dec. 27, 2012, and U.S. patent application Ser. No. 13/730,212, titled "SYSTEMS AND METHODS TO GATHER AND ANALYZE ELECTROENCEPHALOGRAPHIC DATA," filed on Dec. 28, 2012, all of which claim priority to U.S. Provisional Patent Application Ser. No. 61/684,640, titled SYSTEMS AND METHODS TO GATHER AND ANA-LYZE ELECTROENCEPHALOGRPHIC DATA, filed on Aug. 17, 2012, and all of which are incorporated herein by reference in their entireties.

The electrodes 133a-n may have any suitable shape such as, for example, at least a portion of a ring, a ball, a hook and/or an array. Also, in some examples, the electrodes 133a-n, and the strips 104-112 to which the electrodes 133a-n are coupled, have a protective covering such as, for example, a nylon and/or a silver mesh. In some examples, the covering is a stretchable silver-coated nylon mesh. The covering provides additional shielding and protection. In addition, the electrodes 133a-n including the covering may be machine washable.

In the example shown, each of the straps 124-132 is adjustable (e.g., slidable) along the respective spine structures 124-132 and provides a downward forced on the spine structures 124-132 and, thus, the electrodes (e.g., 133a-n) coupled thereto. In the illustrated examples, each of the spine structures 124-132 is comprised of a flexible material such as, for example, plastic, rubber, polyurethane, silicone and/or any other suitable material or combination of materials. The flexibility of the example spine structures 124-132 enables the headset 100 to sit comfortably on the head of a person by adjusting to the shape of the head of the person without applying a discomforting force to the head.

In the example shown, each of the strips 104-112 is removably attached via its ends to the band 102. Specifically, in the example shown, each of the strips 104-112 has a first female connector 134-142 on one end (shown in FIG. 1A) and a second female connector 144-152 on the other end (shown in FIG. 1B). In the example shown, the headset 100 also includes a plurality of male connectors 154-172 slidably coupled to the band 102. Specifically, the headset 100 includes first male connectors 154-162 that detachably mate with respective ones of the first female connectors 134-142 on one side of the head (shown in FIG. 1A), and also includes second male connectors 164-172 that detachably mate with respective ones of the second female connectors 144-152 on the other side of the head (FIG. 1B). The relationships between each of the male and female connectors 134-172 form fasteners (e.g., magnetic fasteners) to removably attach the strips 104-112 to the band 102. More specifically, each of the strips 104-112 is removably coupled to each to the male connectors 154-172 and, thus, also to the band 102. In addition, the illustrated example shows the strips 104-112 adjustably coupled to the band 102 on both the left and right sides of the person's head. In some examples, the strips 104-112 are adjustably coupled to the band 102 on one side and fixedly coupled on the other side.

As shown in FIGS. 1A and 1B, the male connectors 154-172 are slidably connected to the band 102 and can be moved or repositioned along the band 102. In the example shown, the male connectors 154-162 are located on the band 102 on one side of the person's head (shown in FIG. 1A), and the male connectors 164-172 are located on the band 102 on the opposite side of the person's head (shown in FIG. 1B). This arrangement of the male connectors 154-172 enables the strips 104-112 to be disposed over the head of the person and attached on each end to the male connectors 154-172, respectively. In the example shown, the male connectors 154-172 and the female connectors 134-152 are held together by magnetic force (i.e., the male connectors and female connectors form magnetic fasteners). However, in other examples, the male connectors 154-172 and female connectors 134-152 may be coupled together by other fastening mechanisms including, for example, ties, buttons, hooks, snaps, and/or loop and hook fasteners (e.g., Velcro® fasteners).

In the example shown, each of the female connectors 134-152 is also rotatably coupled to its respective male connector 154-172. The male connectors 154-172 are slidable along the band 102, and the strips 104-112 are removably (and rotatably) coupled to the male connectors 154-172. Thus, each of the strips 104-112 is removable, rotatable, adjustable and repositionable along the scalp of a person. Additionally, each of the example strips 104-112 is adjustable independent of each of the other strips 104-112. The assembly of the male connectors 154-172 and the female connectors 134-152 is described in further detail below.

In the example shown, the headset 100 also includes a support 174 (e.g., a central support) that is coupled to a processing unit 176. The central support 174 provides sufficient rigidity to the headset 100 to enable the headset 100 to be easily placed and fitted on a person's head. In addition, each of the strips 104-112 is slidably coupled to and supported by the central support 174. Also, in some examples, the central support communicatively couples the electrodes 133a-n to the processing unit 176. For example, the central support 174 communicatively couples the electrodes of the example strips 104-112 to the processing unit within the processing unit 176 through communication links running through the central support 174. In some examples, each of the strips 104-112 is electrically coupled to the central support 174 via, for example, a connection terminal on the respective spines 114-122 and complementary terminal on the central support 174. In some examples, the complementary terminals on the central support 174 are independently slidable along the central support 174 to facilitate physical adjustment of the strips 104-112 relative to the head of the person. In other examples, the strips 104-112 are wirelessly coupled to the processing unit 176 and/or a remote processor. For example, one or more of the strips 104-112 may include a transmitter to wirelessly transmit signals (e.g., EEG signals) to the processing unit 176. In such examples, the central support 174 supports the strips 104-112 and provides rigidity and structure to the headset 100 but does not function to convey communication signals. In still other examples, the headset 100 does not include the central support 174 and the processing unit 176, and the signals are communicated to a handheld or other remote receiver.

In the illustrated example, the processing unit 176 may be contained in a housing and may include other electrical components for processing signals gathered from the electrodes 133a-n. In some examples, the electrical components are used to, for example, convert the EEG data from analog data to digital data, amplify the EEG data, remove noise from the data, analyze the data, and transmit the data to a computer or other remote receiver or processing unit. In some examples, the processing unit 176 includes hardware and software such as, for example, an amplifier, a signal conditioner, a data processor and/or a transmitter for transmitting signals to a data center or a computer. In other examples, some of the processing occurs at the headset 100 and some processing occurs remotely after the headset 100 transmits data or semi-processed results to a remote site such as, for example, via a wireless connection. As shown in FIG. 1B, the processing unit 176 also includes a connection terminal 178, which may be used, for example, to connect additional electrodes or sensors to the processing unit 176 as discussed in detail below.

Figure 2:
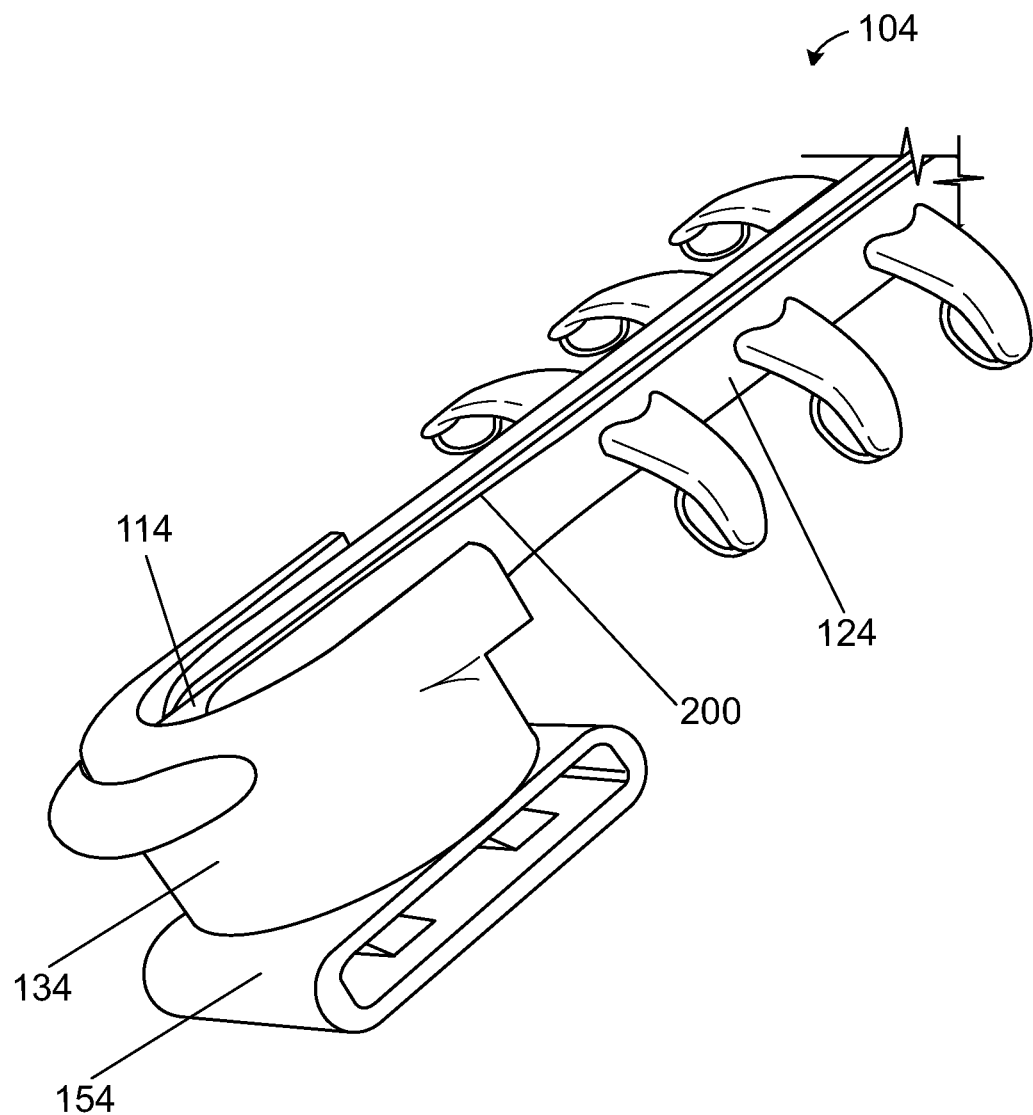
FIG. 2 is an enlarged view of an example fastener of an example one of the strips of the example headset of FIGS. 1A and 1B.

FIG. 2 illustrates the example first female connector 134 of the example first strip 104 coupled to the corresponding example first male connector 154. In some examples, the positions of the male connector 154 and the female connector 134 may be switched such that the female connector 134 is coupled to the band 102 and the male connector 154 is coupled to the strip 104. Also, provided herein is a detailed description related to FIGS. 2-5 of the example male connector 154 and the example female connector 134. However, this disclosure also applies to the example second male connector 164 and the example second female connector 144 on the other side of the first strip 104 and to other strips 106-112 and the corresponding example male connectors 156-162, 166-172 and example female connectors 136-142, 146-152.

As shown, the first strip 104 includes the first spine 114 and the first strap 124. The first strap 124 is disposed within a slot 200 (e.g., a groove, an area between runners or knobs, a slit, etc.) on the first spine 114, and the first strap 124 is slidably adjustable along the first spine 114. In some examples, the first strap 124 is elastic and stretchable. An end of the first strap 124 is slidably coupled to the first female connector 134 (discussed in detail below). In the example shown, the first spine 114 is engaged to the first female connector 134. In other examples, when the first strip 104 is tightened or adjusted on the head of a person, the end of the first strap 124 may extend past the first female connector 134 as discussed in detail below.

In the illustrated example, the first female connector 134 is removably coupled to the first male connect 154 such that the strip 104 may be selectively removed from the male connector 154 and the band 102 and reattached to the first male connector 154 or another one of the male connectors 156-172. The first female connector 134 is also rotatable relative to the first male connector 154 to enable adjustment of the relative angle between the first strip 104 and the band 102. Also, in the example shown, the first female connector 134 and first male connector 154 are magnetically coupled. However, in other examples, the first female connector 134 and the first male connector 154 are attached by other fastening mechanisms.

Figure 3A:
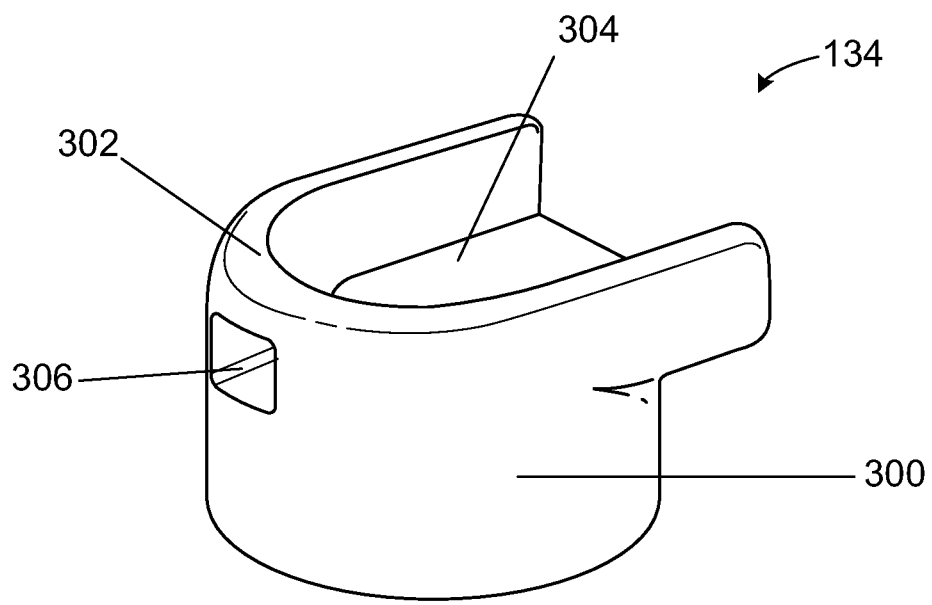
FIG. 3A is a perspective top view of an example female connector of the example fastener of FIG. 2.
Figure 3B:
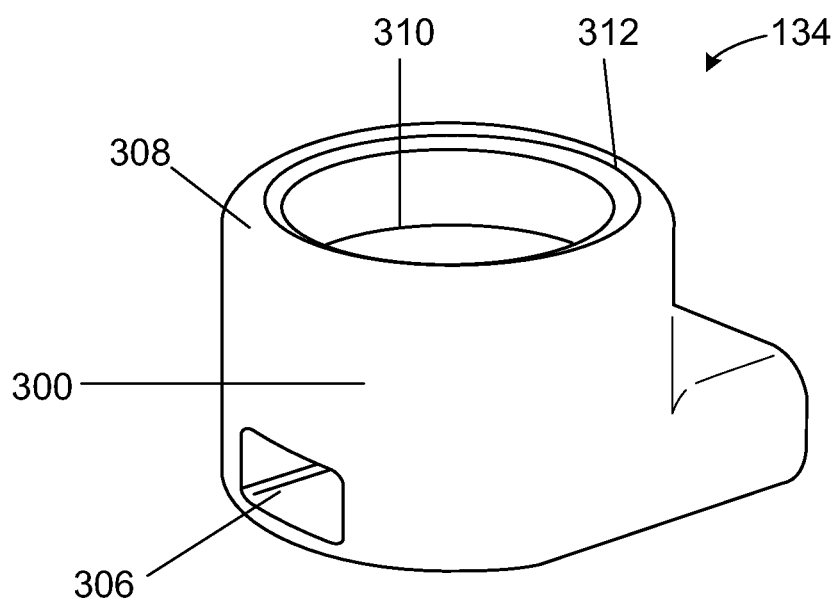
FIG. 3B is a perspective bottom view of the example female connector shown in FIG. 3A.

FIGS. 3A and 3B show top and bottom views of the example first female connector 134. The first female connector 134 includes a body 300 (e.g., a housing) having a top 302.

The top 302 of the first female connector 134 has a slot 304 (e.g., a channel, a groove, an indentation, etc.), which may, for example, receive the end of the first spine 114 (as shown in FIG. 2). In the example shown, the slot 304 has a hemispherical shape that matches a contour or shape of the end of the first spine 114. However, in other examples, the slot 304 has other contours or shapes that may or may not match the shape of the end of a spine. In the example shown, the body 300 of the first female connector 134 also has an aperture 306 (e.g., a hole, an opening, etc.) to receive the strap 124 (shown in FIG. 2). The aperture 306 is formed near an end of the slot 304.

As shown in FIG. 3B, a bottom 308 of the example first female connector 134 has a cup or cavity 310 that is formed by an annular rim or protrusion 312 extending outward from the body 300. In some examples, the cavity 310 is used to retain a magnetic element or a metallic element as described in detail below. In the example shown, the cavity 310 is cylindrical and, thus, has a circular cross-section. However, in other examples, the cup or cavity 310 may have a rectangular, square or otherwise shaped cross-section.

Figure 4A:
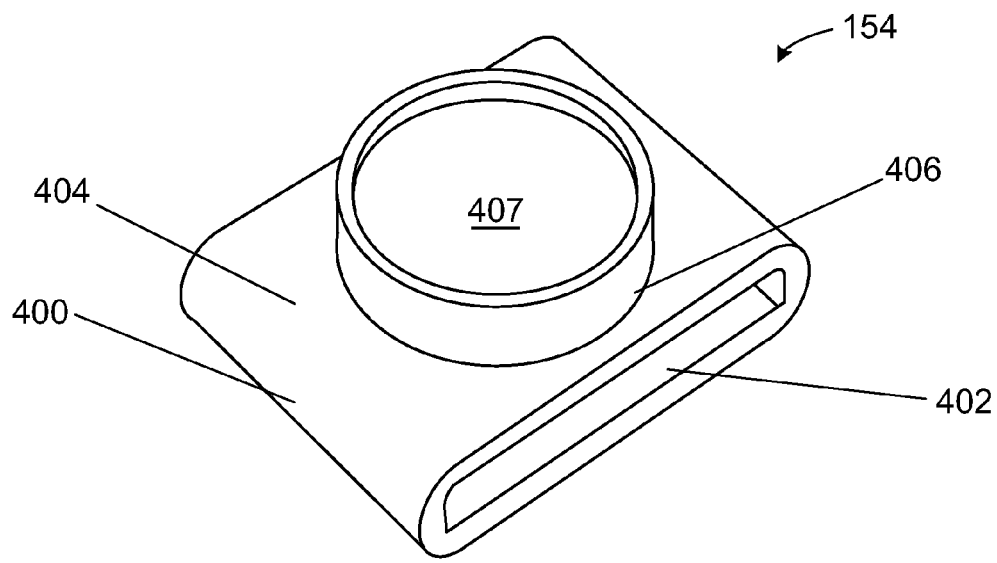
FIG. 4A is a perspective top view of an example male connector of the example fastener of FIG. 2.
Figure 4B:
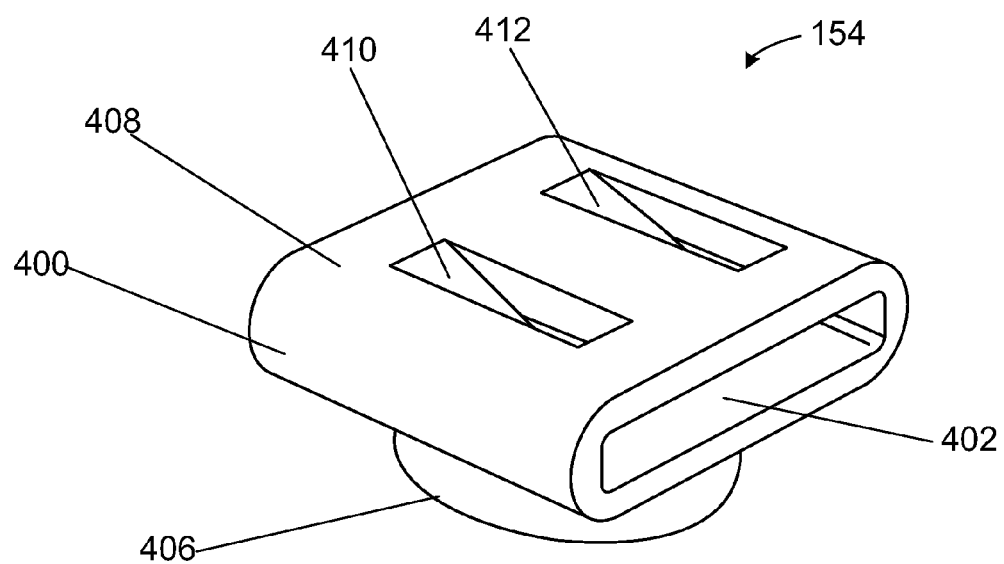
FIG. 4B is a perspective bottom view of the example male connector shown in FIG. 4A.

FIGS. 4A and 4B show top and bottom views of the example first male connector 154. The first male connector 154 includes a body 400 (e.g., a housing) forming an elongated ring. In the example shown, the body 400 has an oval cross-section forming a passage 402 (e.g., an aperture, a hole, an opening, etc.) therethrough. In other examples, the body 400 may have a more circular cross-section, a rectangular cross-section or any other suitable shape. The passage 402 is to receive the band 102 (shown in FIGS. 1A and 1B).

In the example shown, a top side 404 of the example first male connector 154 has an annular rim or protrusion 406 that extends outward from the top side 404 of the body 400 and which forms a cup or cavity 407. A magnet or magnetic plate is disposable in the cavity 407 to facilitate coupling of the example first male connector 154 to the example first female connector 134. In addition, the protrusion 406 is selectively removably insertable into the cavity 310 of the first female connector 134.

A bottom side 408 of the example first male connector 154 has two clips 410, 412. In other examples, there are other numbers of clips such as, for example, one, three, zero, etc. In the example shown, the clips 410, 412 are elongated sections of the body 400 that are displaced (e.g., indented) into the passage 402 of the body 400. In some examples, the clips 410, 412 are spring clips or leaf springs. In other examples, the example first male connector 154 includes one or more clips that are not integrally formed with and that are coupled to the first male connector 154 to the join the male connector 154 and the band 102. The example clips 410, 412 frictionally engage the band 102 (shown in FIGS. 1A and 1B) to hold the first male connector 154 in a specific position along the band 102. The friction may be overcome, for example by human force, to reposition the male connector 154 relative to the band 102. In other examples, other types of clips may be used to resist movement of the male connectors 154-172 along the band 102.

In the example shown, the body 400 of the example first male connector 154 forms a ring. In other examples, the body 400 may include a slit such that the band 102 may be slid through the slit and into the passage 402 of the body 400 to removably couple the first male connector 154 to the band 102.

FIG. 5 illustrates an exploded view of the example first female connector 134 and the example first male connector 154 assembly. As shown, the first strap 124 of the first strip 104 passes through the aperture 306 on the first female connector 134. The end of the strap 124 has a stop 500. When the first female connector 134 reaches the end of the first strap 124, the stop 500 prevents the end of the strap 124 from being pulled through the aperture 306 and, thus, retains the first female connector 134 on the end of the first strip 104. To remove the first female connector 134 from the first strip 104, the stop 500 may be turned sideways such that a longitudinal axis of the stop 500 is aligned with the aperture 306 and is passed through the aperture 306 (i.e., by rotating the stop 500 about 90°. In the example shown, the stop 500 is curved to match the contour of the first female connector 134 to lie flat against the first female connector 134 when the first strap 124 is pulled tight. In the example shown, the stop 500 includes an alignment block 502, which matches the profile (e.g., the shape) of the aperture 306. When the stop 500 engages the first female connector 134, the alignment block 502 partially enters the aperture 306 and maintains the position of the stop 500 secure against the first female connector 134.

In the example shown, the example first female connector 134 includes a first disc 504, and the example first male connector 154 includes a second disc 506. In the example shown, at least one of the first disc 504 and the second disc 506 is a magnet, and the other of the first disc 504 and the second disc 506 is magnetic for interacting with the magnet. The magnetic disc 506 may be, for example a magnetized metallic plate or other material. In other examples, both of the first disc 504 and the second disc 506 are magnets. The first disc 504 is to be disposed within the cavity 310 of the first female connector 134, and the second disc 506 is to be disposed within the cavity 407 of the first male connector 154. The discs 504, 506 may be coupled to their respective connectors 134, 154 by adhesive, friction fit or any other mechanism for coupling two components together. In some examples, the first magnetic disc 504 is coupled to the cavity 407 of the first male connector 154, and the second magnetic disc 506 is coupled to the cavity 310 of the first female connector 134. Also, in some examples, the female connector 134 or at least a portion of the first female connector 134 (e.g., the rim 312) comprises a magnetic material. Similarly, in some examples, the first male connector 154 or at least a portion of the first male connector 154 (e.g., the lip 406) comprises a magnetic material.

The magnet or the first disc 504 and the magnetic disc or the second disc 506 cause the example first female connector 134 and the example first male connector 154 to attract each other and form a magnetic bond. Specifically, when engaged, as shown in FIG. 2, the protrusion or lip 406 of the first male connector 154 is releasably inserted into the cavity 310 of the first female connector 134 and the attraction (e.g., magnetic force) between the first disc 504 and the second disc 506 holds the example first female connector 134 and the example first male connector 154 together. The complementary circular profile of the cavity 310 of the female connector 134 and the circular shape of the protrusion 406 of the male connector 154 enable the female connector 134 to be rotated relative to the first male connector 154, which allows the end of the strip 104 to be further adjusted (e.g., angled) on the head of a person relative to the band 102. In other examples, the cavity 310 of the first female connector 134 and the protrusion 406 of the male connector 154 may have other shapes including square or rectangular profiles. Also, in some examples, the first male connector 154 and the first female connector 134 may fit together as gears with teeth or cogs that engage in a plurality of discrete positions.

In some examples, when adjusting the first strip 104 on the headset 100, the first female connector 134 is coupled to the first male connector 154 and the stop 500 is engaged with the first female connector 134 (e.g., the position shown in FIG. 2).

In some examples, the first strip 104 is adjusted, for example, tightened, such that a portion of the first strap 124 extends beyond the first female connector 134, and the stop 500 is not positioned against the first female connector 134. In some examples, the aperture 306 may include protrusions (e.g., knobs, pins) that engage the side of the first strap 124 to restrict movement (e.g., via friction) of the strap 124 through the aperture 306. In such examples, the first strip 104 may be used on different sized heads and may be adjusted accordingly. For example, in the case of a smaller head, the example first female connector 134 is attached to the example first male connector 154 and the first strap 124 may pulled through the aperture 306 until the first strap 104 applies an appropriate pressure against the head of the person. Therefore, the effective length of each one of the example strips 104-112 may be changed.

In some examples, different size strips are manufactured to accommodate different size heads. For example, a person with a head measuring 62-64 centimeters (cm) may use a headset with strips measuring a first length, and a person with a head measuring 58-62 cm may use a headset with strips measuring a second length, shorter than the first length. Therefore a plurality of different sized strips may be used with a headset to comfortably accommodate any sized/shape head.

In some examples, when assembling example headset 100, the example strips 104-112 are coupled to the male connectors 154-172 on the band 102 and then the headset 100 is placed on the head of a person. The central support 174 and the processing unit 176 may also be attached to the strips 104-112 prior to placing the headset 100 on the head of a person. In other examples, the band 102 is placed on the head of a person (e.g., by clipping two ends of the band 102 together or stretching an elastic band over the head) and then each of the example strips 104-112 is individually coupled (e.g., magnetically) to the male connectors 154-172 on the band 102. The male connectors 154-172 are slidable along the band 102 to adjust the location of the strips 104-112 and, thus, the respective arrays of electrodes on each of the strips 104-112 relative to the head of the person. The example female connectors 134-152 are also rotatable on their respective example male connectors 154-172, further allowing the strips 104-112 to be positioned (e.g., angled) on the head of a person. The magnetic coupling between the male and female connectors 134-172 also provides a safety function by enabling example the strips 104-112 to easily be disconnected from the band 102 if too much force is exerted on the band 102. For example, if the strips 104-112 of the headset 100 are snagged or caught on a foreign object, the magnetic force of the male and female connectors may be overcome, and the example strips 104-112 disconnect from the band 102.

Figure 6:
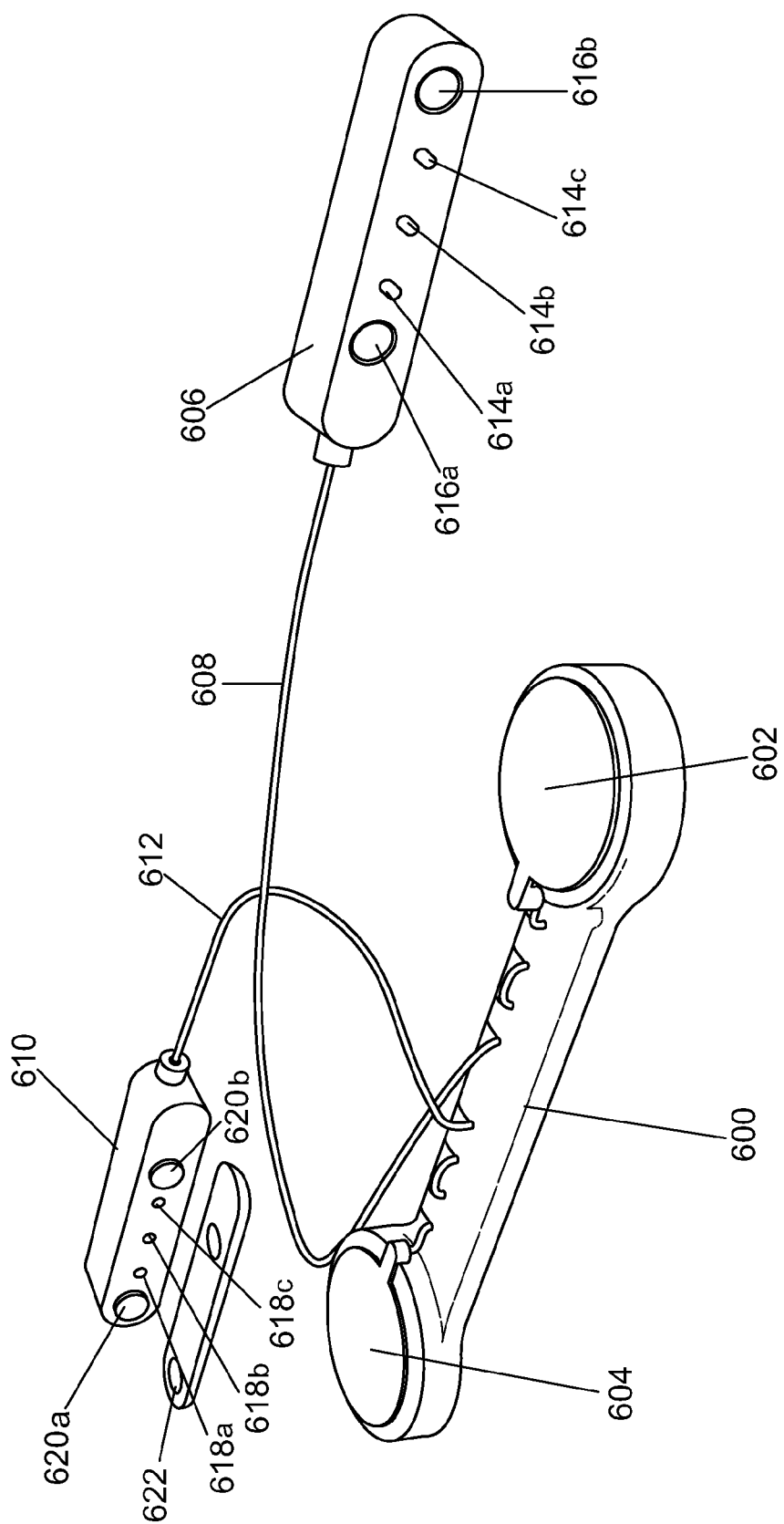
FIG. 6 illustrates a perspective view of an example electrode clip in accordance with the teachings of this disclosure.

FIG. 6 illustrates an example clip 600 for housing or retaining one or more electrodes such as, for example, a reference or ground electrode. The clip 600 interfaces with a person's skin by, for example, clipping to the skin of a person (e.g., on an earlobe) or being placed against the skin (e.g., on a forehead). In some examples, an electrode is used as a reference or ground electrode to provide a reference signal for comparing with the EEG signals gathered from other parts of the person's head by, for example, the headset 100 shown in FIGS. 1A and 1B. A reference or ground electrode is positioned at a point on the person's body that has minimal or no EEG activity or other artifacts and/or noise such as, for example, those indicative of muscle contractions or blood flow. In some examples, the reference or ground electrode is connected to the earlobe and/or at the tip of a person's nose.

In the example shown, the clip 600 includes a first electrode 602 and a second electrode 604. In some examples, one or both of the electrodes 602, 604 is a reference or ground electrode. In other examples, one or both of the electrodes may be used to gather other EEG signals from a person's head. In still other examples, one of the electrodes is used for shielding while the other electrode may be used as a reference or ground electrode or to gather EEG data from the person's head.

As shown in FIG. 6, the first electrode 602 is coupled to a first terminal 606 via a first wire 608, and the second electrode 604 is coupled to a second terminal 610 via a second wire 612. In the example shown, the first and second electrodes 602, 604 are similar, and the first and second terminals 606, 610 are similar. Thus, the description of the features of one of the electrodes 602, 604 applies to the other one of the electrodes 602, 604, and the description of the features of one of the terminals 606, 610 applies to the other one of the terminals 606, 610. In FIG. 6, one side of a terminal is shown on the first terminal 606 and the other side of a terminal is shown on the second terminal 610 for illustrative purposes.

The first and second terminals 606, 610 couple the wires 608, 612 and, thus, the electrodes 602, 604 to the example processing unit 176 (FIGS. 1A and 1B). As shown in reference to the first terminal 606, which also corresponds to the side of the second terminal 610 not shown in FIG. 6, the first terminal 606 has a first connector including three prongs or pins 614a-c protruding from the side of the first terminal 606. Additionally, the first terminal 606 has two magnetic connectors or pads 616a, 616b. The pins 614a-c are aligned along a longitudinal axis of the first terminal 606 with the first magnetic pad 616a on one end and the second magnetic pad 616b on the other end. The pins 614a-c are used to transfer signals/data (e.g., EEG signals) gathered from the electrode 602 to the processing unit 176. As shown in FIG. 1B, the processing unit 176 includes the receiver 178 (e.g., a terminal), having three apertures 180a-c and two magnetic pads 182a, 182b. Similar to the connectors of the first and second terminals 606, 610, the receiver 178 has matching components such that the three pins 614a-c can be plugged into the three apertures 180a-c to mechanically and electrically couple the terminal 606, 610 to the processing unit 176. In addition, the magnetic pads 616a, 616b of the terminal 606 couple to the magnetic pads 182a, 182b of the processing unit 176 to releasably secure the terminal 606 to the processing unit 176. In some examples, the receiver 178 on the processing unit 176 is used for attaching other electrodes or physiological/biological measurement devices (e.g., an EKG sensor, an eye tracking sensor, etc.). The additional devices may include terminals having similar connectors or terminals (e.g., apertures and pins, connection points) that may be attached to the processing unit 176 or to other terminals attached to the processing unit 176 as discussed below.

As shown in FIG. 6 in reference to the second terminal 610, which also corresponds to the side of the first terminal 606 not shown in FIG. 6, the second terminal 610 includes multiple channels or apertures 618a-c and two magnetic pads 620a, 620b. The terminals 606, 610 may be stacked, such that two or more terminals may be plugged into each other and coupled as a group to the processing unit 176. For example, the second terminal 610 may be coupled to the processing unit 176 by coupling pins and magnetic pads on the second terminal 610 (similar to the pins 614a-c and the magnetic pads 616a, 616b on the first terminal 606 shown in FIG. 6) to the apertures 180a-c and magnetic pads 182a, 182b of the receiver 178 of the processing unit 176 (shown in FIG. 1B). The apertures 618a-c of the second terminal 610 can receive the pins 614a-c from the first terminal 606 to stack the first and second terminals 606, 610 and couple the first terminal 606 to the processing unit 176 via the second terminal 610. The magnetic pads 616a, 616b on the first terminal 606 align with and, thus, can engage the magnetic pads 620a, 620b as shown on the second terminal 610 and the magnetic force releasably secures the first and second terminal 606, 610. A third terminal may be stacked on the first terminal 606 in a similar manner. A fourth terminal also may be coupled and so forth. In the illustrated example, the terminals 606, 610 include a cap or lid 622 to protect the apertures 618a-c and magnetic pads 620a, 620b from the environment.

Figure 7:
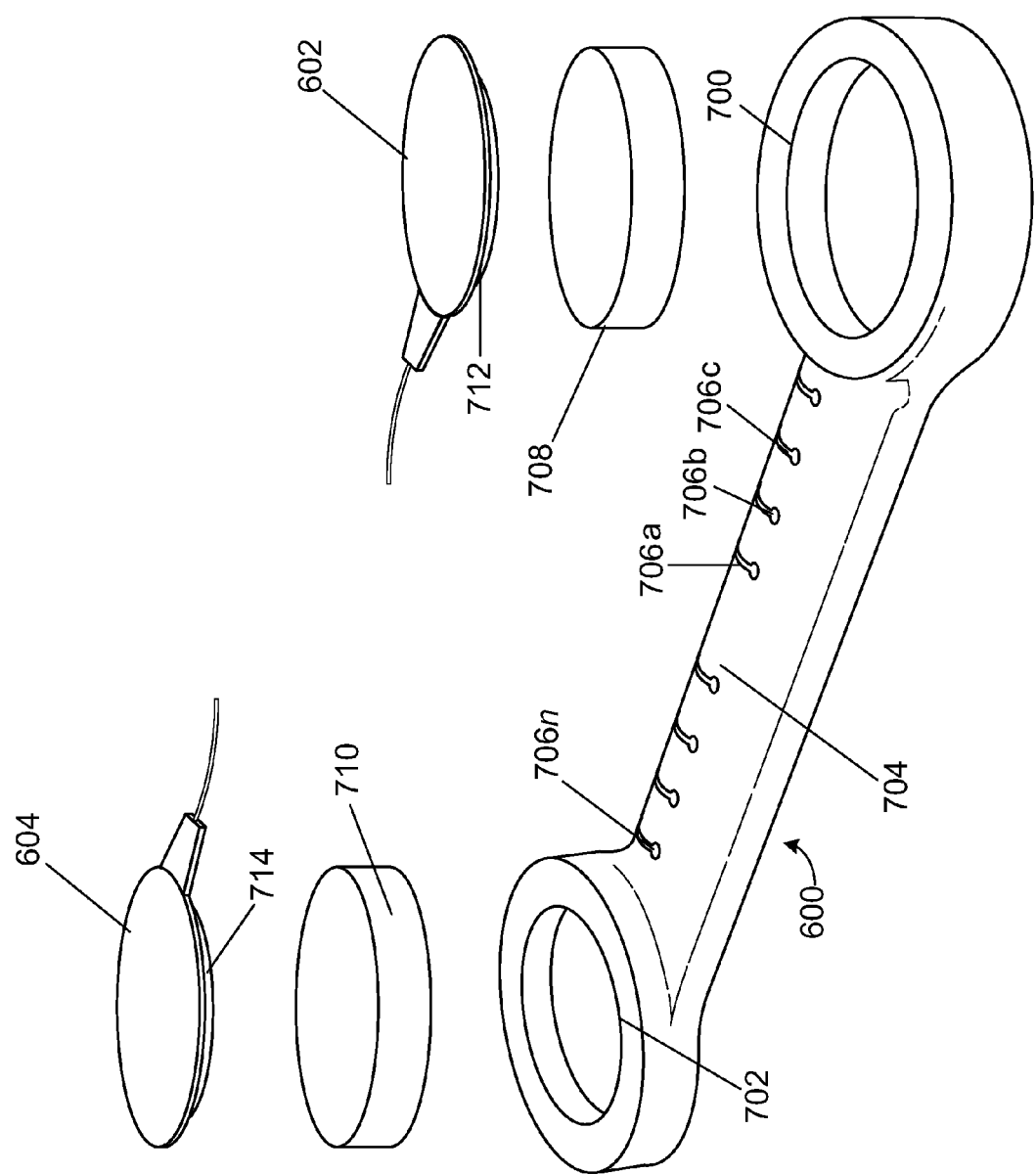
FIG. 7 illustrates an exploded view of the example electrode clip shown in FIG. 6.

FIG. 7 shows an exploded view of the example clip 600. The clip 600 includes a first cavity or cup 700 at a first end and a second cavity or cup 702 at a second end, which are coupled by an intermediary portion or body 704. In the example shown, the body 702 includes a plurality of slits 706a-n, which retain one or more wires such as, for example, the first wire 608 and/or the second wire 612. The slits 706a-n secure the wires 608, 612 (FIG. 6) leading to electrodes 602, 604 to the body 704 of the clip 600, which enhances safety by holding the wires 602, 604 close to the clip 600, thereby decreasing the likelihood of the wires 602, 604 being snagged on another object such as, for example, another portion of the headset 100 or the person's hand. In addition, if one or both of the wires 608, 612 (FIG. 6) is caught or snagged on an object, the force on the wire 608, 612 removes the clip 600 from the body or skin of the person, rather than pulling directly on the electrode, which may be against the skin of a person and could potentially cause pain.

In the example shown, the body 704 and the cups 700, 702 may be formed as unitary piece (e.g., molded as one component). In other examples, the body 704 and the cups 700, 702 are made of separate pieces and coupled together to form the clip 600. Also, in some examples, the first and second cups 700, 702 include metallic rings or cups molded (e.g., encased) inside the cups 700, 702 (e.g., plastic is poured over the metallic cups). The metallic cups provide shielding against line noise and other type(s) of noise.

A first disc 708 is disposed in the first cup 700 and a second disc 710 is disposed in the second cup 702. In some examples, the one or both of the discs 708, 710 are magnetic such as, for example, comprising a metallic material. In some examples, the discs 708, 710 are magnetically attracted to the metallic cups molded within the first and second cups 700, 702, such that when the discs 708, 710 are placed in the first and second cups 700, 702, a magnetic force releasably secures the discs 708, 710 in the respective cup 700, 702.

In the illustrated example, the clip 600 includes the first electrode 602 disposed in the first cup 700 and the second electrode 604 disposed in the second cup 702. In some examples, the first electrode 602 includes a first flange 712 to hold such as, for example, via a friction fit, the first electrode 602 in the first cup 700. The first flange 712 engages an undercut or a wall of the first cup 700. Similarly, the second electrode 604 includes a second flange 714 to hold the second electrode 604 in the second cup 702. In some examples, an edge of the electrodes 602, 604 provide the friction to secure the electrodes 602, 604 in place.

In some examples, the electrodes 602, 604 do not include flanges and are, for example, flat or cup-shaped on the bottom. In some examples, the first and second electrodes 602, 604 are made of a metallic material and/or are coated (e.g., anodized or plated) with a metallic material (e.g., silver, gold, etc.). In such examples, the metallic electrodes and/or the coatings are magnetically attracted to the discs 708, 710, and the magnetic force releasably holds the electrodes 602, 604 in the respective cups 700, 702.

In the example shown, the clip 600 has two electrodes 602, 604. However, in other examples only one electrode may be used in one of the cups 700, 702. In such examples, the cups 700, 702 include both discs 708, 710 to create a magnetic force and hold the clip against the body (e.g., skin, an ear lobe, etc.) of a person.

As mentioned above, the example clip 600 may be coupled against a person's forehead or to a person's earlobe or nose. When the example clip 600 is to be coupled to the forehead, the clip 600 is in the flat or substantially flat orientation shown in FIGS. 6 and 7, with the first and second cups 700, 702 facing the same direction. In this example, the clip 600 may be coupled to the band 102 (FIGS. 1A and 1B) to hold the clip 600 on the forehead.

Figure 8A:
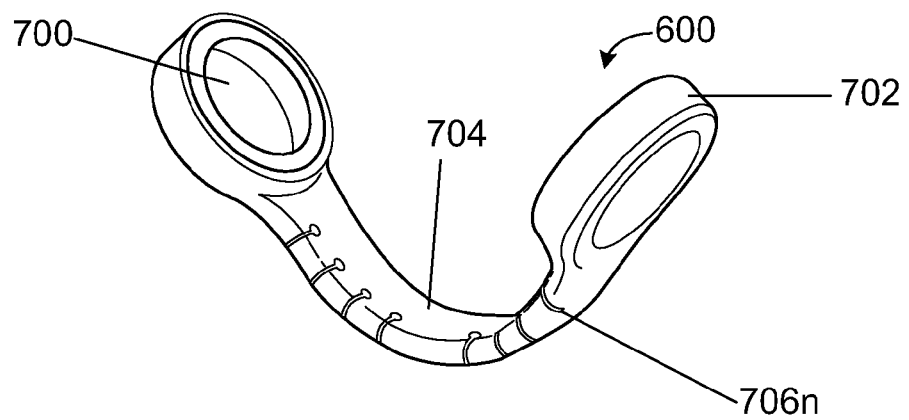
FIG. 8A is a perspective view of the example electrode clip of FIG. 6 partially bent around a midpoint.
Figure 8B:
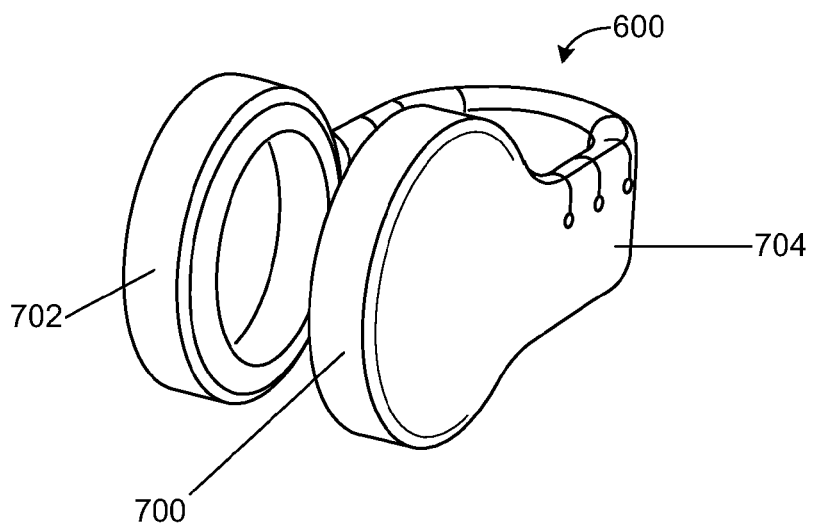
FIG. 8B is a perspective top view of the example electrode clip of FIG. 6 bent around a midpoint.
Figure 8C:
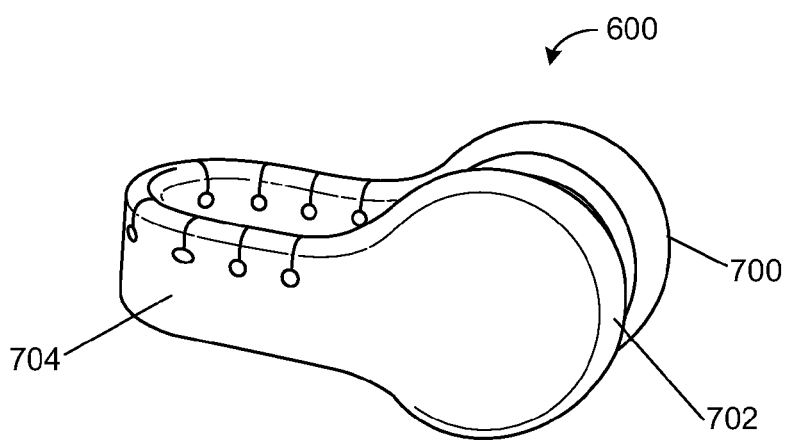
FIG. 8C is a perspective side view of the example clip of FIG. 6 bent around a midpoint.

To couple the example clip 600 to the earlobe or nose, the body 704 of the clip 600 may be folded or bent such the first cup 700 and the second cup 702 are moved toward each other in an opposed orientation. FIGS. 8A, 8B, and 8C illustrate different views of the clip 600 in bent and partially bent configurations. For example, the body 704 may be made of, for example, a plastic, a rubber, a thermoplastic elastomer, silicone and/or any other material capable of being bent multiple times without fracturing. In some examples, the body 704 is pliable such that the clip 600 is configurable between the flat position of FIG. 6 and the bent position of FIGS. 8B and 8C such that the clip 600 may be used on the forehead, then on the earlobe, then back on the forehead as desired.

In some examples, the discs 708, 710 (e.g., magnetic plates, metal plates) disposed within the cups 700, 702 cause the cups 700, 702 to magnetically attract each other and, thus, the clip 600 remains in a closed position or bent position (e.g., the position shown in FIGS. 8B and 8C). The magnetic force is sufficient to extend through human tissue to hold the clip 600 to the earlobe. Also, in some examples, the clip 600 may include only the second disc 710 coupled to the second cup 702. When bent towards each other, the metallic coating on the first electrode 602 is magnetically attracted to the second disc 710, which holds the clip 600 on the earlobe. In other examples, the first cup 700 may be metallic or otherwise magnetic, and the first cup 700 is magnetically attracted to the second disc 710, which holds the clip 600 on the earlobe regardless of the composition of the electrode 602.

Figure 9:
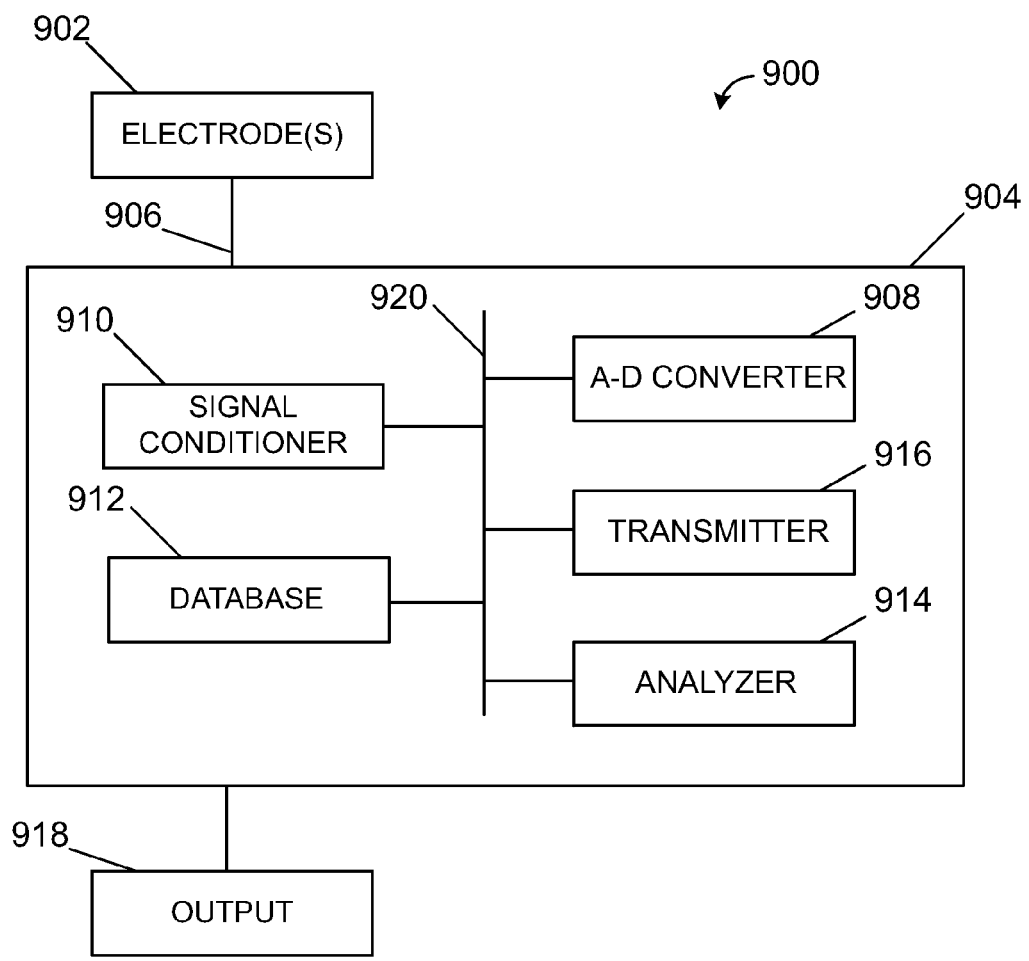
FIG. 9 is a block diagram of an example circuit from the headset in FIG. 1.

FIG. 9 is a block diagram of an example processing system 900 for use with the example headset 100. The example system 900 includes a plurality of electrodes 902 such as, for example, the electrodes 133*a*-*n* of the example headset 100. The electrodes 902 are coupled, for example, to a headset to be worn on a head of a subject. In the example headset 100 disclosed above, the headset 100 includes the band 102 to be worn on a head of a person and the plurality of removable and adjustable strips 104-112 that extend over the head of the person when attached to the band 102. In some examples, each of the strips 104-112 includes their respective strap 114-122 and respective spine structure 124-132 having a plurality of electrodes (e.g., the electrodes 133*a*-*n*). In some examples, each end of each one of the strips 104-112 is removably and rotatably fastened (e.g., magnetically) to the band 102 such that the electrodes can be moved to different positions on the head and/or removed from the band 102. In some examples, the headset 100 includes numerous channels of electrodes such that multiple (e.g., 2000 or more) electrodes are included in the example system 900. In addition, in some examples, the pressure applied on the head by each electrode may be adjusted by adjusting the strap associated with each of the strips 104-112. In other examples, different size strips may be added and/or removed that fit comfortably over the head of the person.

In some examples, one or more electrodes 902 are coupled to a body of a person via a clip such, as for examples, the clip 600 shown in FIG. 6. In some examples, the clip retains one or two electrodes and the clip is laid flat against the skin (e.g., the forehead) of the person to engage the electrodes to the skin. In some examples, the clip is attached to the band of the headset. In the example clip 600 disclosed above, the clip 600 includes the body or intermediary portion 704 that is flexible and foldable. In some examples, the clip 600 includes one or two plates or discs (e.g., the discs 708, 710) that are attracted (e.g., magnetically) to each other such that a bent or folded clip 600 is releasably held onto the skin of a person such as, for example, the earlobe or the nose of a person. In some examples, the electrodes 902, which may be, for example, the electrodes 602, 604, are used to provide a ground or reference signal. In some examples, the electrodes are used as a shield.

The example electrodes 902 may also be adjustably mechanically coupled, such as for example, via the strips to the band where the magnetic fasteners are supported to releasably hold the strips and, thus, the electrodes 902 in different positions along the scalp. An example magnetic fastener includes the male connector and female connector assembly disclosed above.

The electrodes 902 are also communicatively coupled to a processing unit 904 (e.g., the processing unit 176 of the headset 100 shown in FIGS. 1A and 1B) via a communication link 906, which may be for example a wired or wireless communication link including, for example, the PCB communication channels disclosed above. The communication link 906 may be, for example, incorporated in the central support 174 of the headset 100. In some examples, the strips (and their respective electrodes) are slidably coupled along the central support. In some examples, the central support includes communication links (e.g., wires) to communicatively coupled each of the strips to the housing. The example processing unit 904 includes an analog-to-digital converter 908, a signal conditioner 910, a database 912, an analyzer 914 and a transmitter 916.

The analog-to-digital converter 908 converts the analog signals received at the electrodes 902 to digital signals. In some examples, the analog-to-digital converter 908 is located in the processing unit 904 in the housing of the headset. In other examples, the analog-to-digital converter 908 comprises multiple A-D converters located to service individual or sets of the electrodes to convert the signals as close to the source as possible, which may further reduce interference.

The signal conditioner 910 of the illustrated example prepares the gathered signals so that the data is in a more usable form. For example, the signal conditioner 910 may include an amplifier to amplify the signal to a more detectable level. In addition, the signal conditioner 910 may include a filter to remove noise from the signal. The filter may also be used as a bandpass filter to pass one or more frequency bands and/or manipulate select bands depending on the desired processing and/or analysis. In some examples, each of the electrodes 902 may include a signal conditioner at or near the electrode 902. The example signal conditioner 910 may include hardware and/or software to execute a signal conditioning method. In some examples, the signal conditioner includes a detrending unit to compensate for electrode polarization, in which there is slow movement of the voltage signal unrelated to brain wave activity due to polarization of the electrodes. The example processing unit 904 also provides signal processing that may include hardware and/or software to execute Fast Fourier Transform (FFT) calculations, coherence measurements and/or custom adaptive filtering.

The analyzer 914 is to analyze the data gathered from the electrodes 902 and processed by the analog-to-digital converter 908 and the signal conditioner 910 in accordance with one or more analysis protocols depending on the desired study. For example, in accordance with some studies, the analyzer 914 may process the data to determine one or more of a subject's mental state, physiological state, attention, resonance or memory, emotional engagement and/or other suitable characteristics of the subject.

The transmitter 916 communicates the data at any stage of processing and/or the results of the analysis from the analyzer 914 to an output 918. The output 918 could be a handheld device, an alarm, a display screen on the headset, a remote server, a remote computer and/or any other suitable output. Data transmission may be implemented by Bluetooth transmission, wi-fi transmission, ZiGBee transmission and/or encryption before transmission. In the illustrated example, the database 912 stores all data gathered streams. The streams can be buffered for streaming or stored on-board (i.e., at the headset) for periodic or aperiodic uploads during, for example, low-activity periods.

The processing unit 904 components 908-916 are communicatively coupled to other components of the example system 900 via communication links 920. The communication links 920 may be any type of wired connection (e.g., a databus, a USB connection, etc.) or a wireless communication mechanism (e.g., radio frequency, infrared, etc.) using any past, present or future communication protocol (e.g., Bluetooth, USB 2.0, USB 3.0, etc.). Also, the components of the example system 900 may be integrated in one device or distributed over two or more devices.

While example manner of implementing the system 900 has been illustrated in FIG. 9, one or more of the elements, processes and/or devices illustrated in FIG. 9 may be combined, divided, re-arranged, omitted, eliminated and/or implemented in any other way. Further, the example processing unit 904, the example signal conditioner 910, the example A/D converter 908, the example database 912, the example transmitter 916, the example analyzer 914, the example output 918 and/or, more generally, the example system 900 of FIG. 9 may be implemented by hardware, software, firmware and/or any combination of hardware, software and/or firmware. Thus, for example, any of the example processing unit 904, the example signal conditioner 910, the example A/D converter 908, the example database 912, the example transmitter 916, the example analyzer 914, the example output 918 and/or, more generally, the example system 900 of FIG. 9 could be implemented by one or more analog or digital circuit(s), logic circuits, programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the example processing unit 904, the example signal conditioner 910, the example A/D converter 908, the example database 912, the example transmitter 916, the example analyzer 914 or the example output 918 is/are hereby expressly defined to include a tangible computer readable storage device or storage disk such as a memory, a digital versatile disk (DVD), a compact disk (CD), a Blu-ray disk, etc. storing the software and/or firmware. Further still, the example system 900 of FIG. 9 may include one or more elements, processes and/or devices in addition to, or instead of, those illustrated in FIG. 9, and/or may include more than one of any or all of the illustrated elements, processes and devices.

Figure 10:
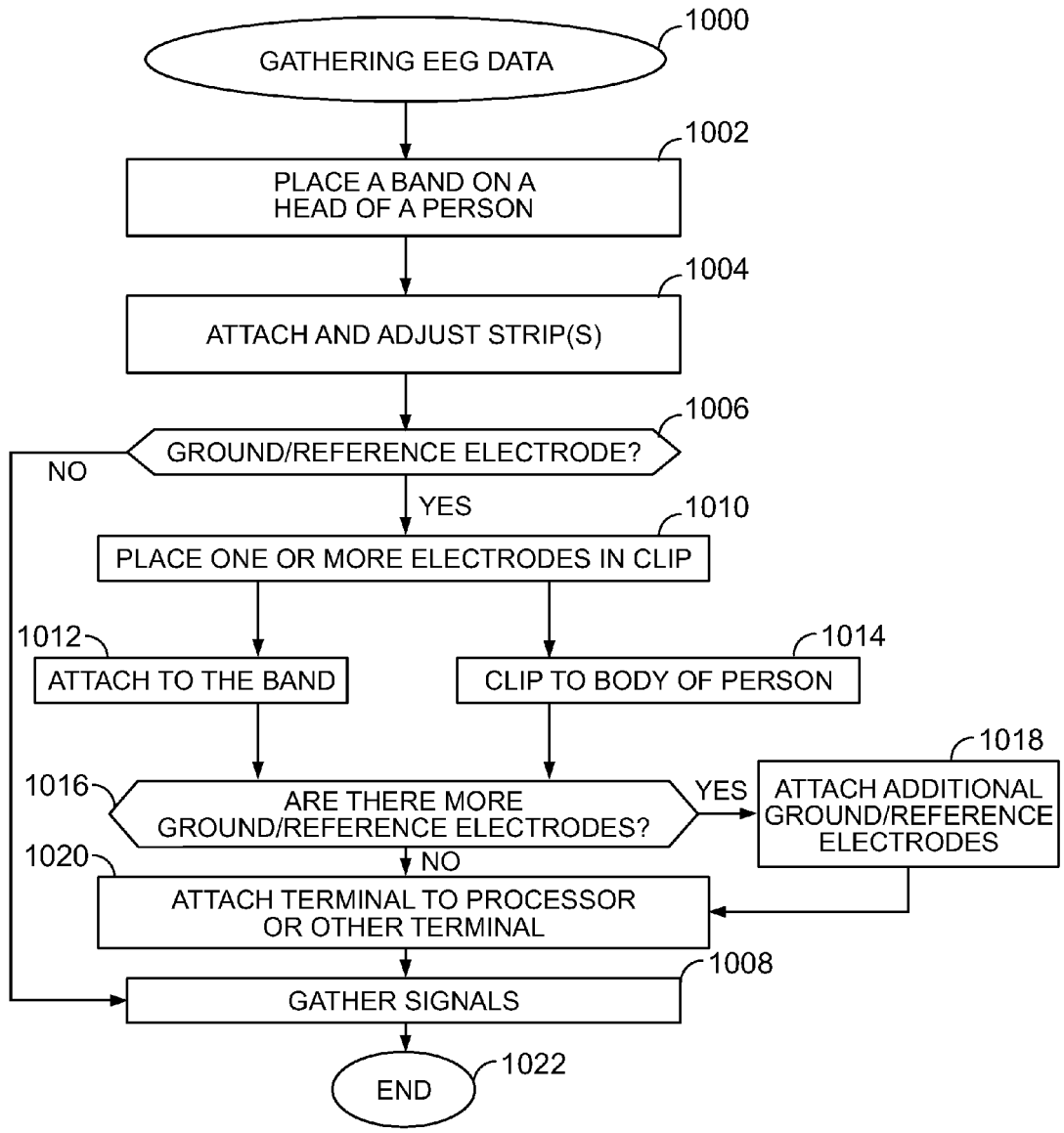
FIG. 10 is a flowchart representing example instructions, at least some of which are machine readable, for implementing an example headset with removable and adjustable strips and gathering EEG data in accordance with the teachings of this disclosure.
Figure 11:
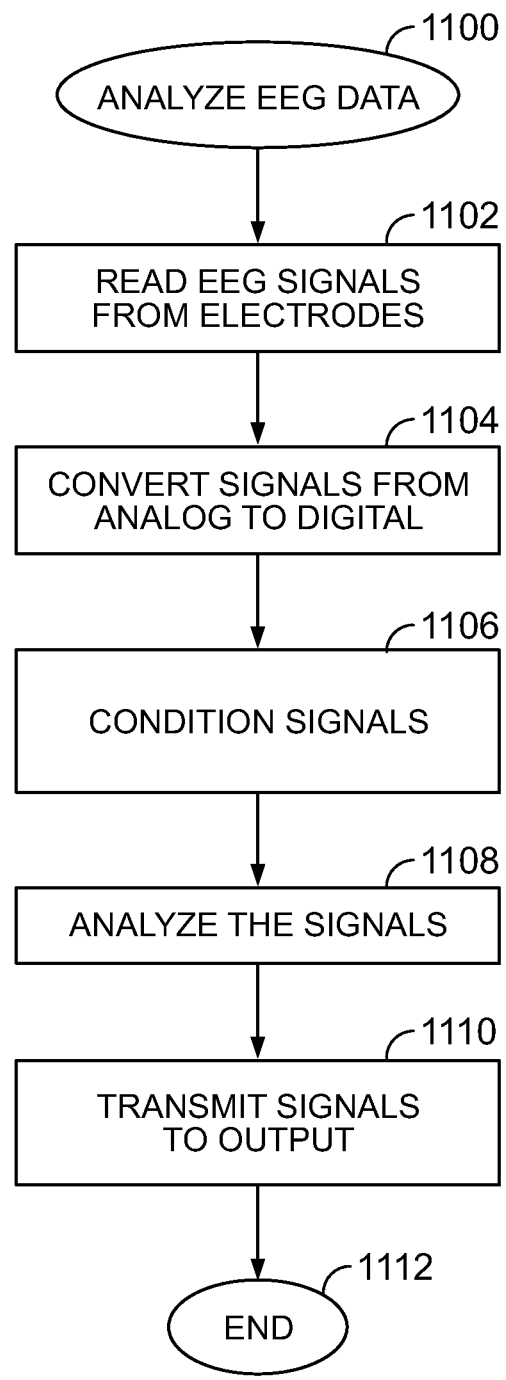
FIG. 11 is a flowchart representative of example machine readable instructions for analyzing EEG data gathered from an example headset with removable and adjustable strips in accordance with the teachings of this disclosure.

Flowcharts representative of example instructions, at least some of which are machine readable, for implementing the headset 100 and/or system 900 of FIGS. 1A-9 are shown in FIGS. 10 and 11. In this example, the machine readable instructions comprise a program for execution by a processor such as the processor 1212 shown in the example processing platform 1200 discussed below in connection with FIG. 12. The program may be embodied in software stored on a tangible computer readable medium such as a CD-ROM, a floppy disk, a hard drive, a digital versatile disk (DVD), or a memory associated with the processor 1212, but the entire program and/or parts thereof could alternatively be executed by a device other than the processor 1212 and/or embodied in firmware or dedicated hardware. Further, although the example program is described with reference to the flowcharts illustrated in FIGS. 10 and 11, many other methods of implementing the example headset 100 and/or example system 900 may alternatively be used. For example, the order of execution of the blocks may be changed, and/or some of the blocks described may be changed, eliminated, or combined.

As mentioned above, the example process of FIG. 11 and at least a portion of the example process of FIG. 10 may be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals. As used herein, "tangible computer readable storage medium" and "tangible machine readable storage medium" are used interchangeably. Additionally or alternatively, the example process of FIG. 11 and at least a portion of the example process of FIG. 10 may be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable device or disk and to exclude propagating signals. As used herein, when the phrase "at least" is used as the transition term in a preamble of a claim, it is open-ended in the same manner as the term "comprising" is open ended.

FIG. 10 is a flowchart illustrating an example process of gathering EEG data (block 1000) that may be implemented, for example, with the headset 100 disclosed herein. The example process beings by placing a band on a head of a person (block 1002) such as, for example, the band 102 shown in FIGS. 1A and 1B. The example band, as disclosed above, is elastic and may be stretched over the head of the person. In some examples, the band includes a connection point such as, for example, a clip that joins two ends of the band.

The example process 1000 includes attaching and adjusting one or more strips (block 1004). In some examples, each strip includes a plurality of electrodes and each strip is removably and adjustably coupled on each end to the band such that the strip is disposed over the head of the person. The example headset 100 disclosed above includes the plurality of attachable/detachable strips 104-112 each having their respective spine structures 124-132 and straps 114-122. The spine structures 124-132 include an array (e.g., one or more) of electrodes for gathering signals along the scalp of the person. The headset 100 may include two, three, four or ten or more individual strips 104-112. The strips 104-12 are fastened (e.g., magnetically) at each end to the band 102 and are disposed over the head of a person. In some examples, the strips 104-112 include the female connectors 134-152 that magnetically couple to the male connectors 154-172, which in turn slidably couple to the band 102.

In some examples, each of the male connectors 154-172 includes a passage that allows the male connectors 154-172 to slide along the band 102 and, thus, the ends of the strips 104-112 are also slidable along the band 102 when connected to the male connectors 154-172, which laterally adjusts the respective strips 104-112. The female connectors 134-152 are also rotatable on the male connectors 154-172 to adjust an angle of the respective strips 104-112 relative to the band 102. Therefore, the strips 104-112 may be independently adjusted on the head of a person laterally and/or rotationally to a specific location where EEG readings are desired and/or are most effective. In some examples, the headset 100 includes the central support 174, and adjusting the strip 104-112 includes independently sliding the strip 104-112 along the central support 174.

In some examples, only one strip is attached to the band and adjusted. If additional strip(s) are desired, then more strip(s) may be added as needed and/or desired (block 1004). In the example headset described above, five strips are utilized to gather EEG signals along the scalp. In other examples, three, four or ten or more strip may be attached to the band. In some examples, the headset is pre-assembled and the example process 1000 includes placing the headset on the head of the person and adjusting the strips such as, for example, laterally and/or rotationally adjusting the strips. With a pre-assembled headset, attachment of the strips may occur before the example EEG data gathering process 1000. For example, a manufacturer may attach the strips.

The example process 1000 includes determining whether a reference or ground electrode separate from the headset is to be used (block 1006). If a reference or ground electrode separate from the headset is not to be used, then signals are gathered (block 1008) from the one or more of the strip(s) that are coupled to the headset.

If a reference or ground electrode separate from the headset is to be used (block 1006), then the example process 1000 includes placing one or more electrodes in a clip (block 1010) such as, for example, the example clip 600 disclosed above. In the example clip 600 disclosed above, a first electrode is placed in one of the cups 700, 702 and a second electrode may be placed in the other cup 700, 702.

The example process 1000 includes attaching the clip to the band (block 1012) or clipping the clip to a body of the person (block 1014). In the example clips 600 disclosed above, the clip 600 includes the flexible body 704 that may be laid flat or bent. In the flat position, the clip 600 (and the one or two electrodes) may be attached to the band 102. In some examples, the clip 600 is attached at a front of the band 102 such that the electrodes (e.g., the electrodes 602, 604) lie against the forehead of the person. In other examples, the clip 600 may be used to clip onto the skin or a portion of the person's body. In such examples, the discs 708, 710 in the cups 700, 702 may be magnets and/or metallic plates are arranged to attract each other. The body 704 of the clip 600 is flexible and as the ends of the clip 600 attract each other (e.g., via magnetic force), the clip 600 may be clipped on the skin or body of a person such that the electrodes 602, 604 are in contact with the skin. In some examples, the clip 600 is clipped onto an earlobe of the person. In some examples, two electrodes 602, 604 are used in the clip 600 and, therefore, two reference or ground signals are gathered from the clip 600. In some examples, the electrodes 602, 604 are not reference or ground electrodes, but are utilized to gather additional EEG signals from additional regions on the person's body (e.g., the forehead). In some examples, one of the electrodes 602, 604 is used as a shield for the other electrode in the clip 600.

The example process 1000 also includes determining if additional ground or reference electrodes are to be used (block 1016). If it is determined that additional ground or reference electrodes are required, then additional clips can be used to attach the ground or reference electrodes to the body of the person (e.g., attached to the band, attached to the earlobe) (block 1018).

The example process 1000 also includes attaching terminals, to which the electrodes are coupled to a processing unit or to another terminal (block 1020). For example, in the examples disclosed above, the ground or reference electrodes 602, 604 are coupled to terminals 606, 610, which are used to couple the electrodes 602, 604 to the processing unit 176 on the headset 100. The example terminals 606, 610 disclosed above include fasteners such as, for example, the pins 614a-c, the magnetic pads 616a, 616b, 620a, 620b, and apertures 618a-c to enable the attachment disclosed above. In some examples, the terminals are pre-attached to the processing unit and/or another terminal.

In addition, the example process 1000 includes gathering signals from the electrodes of the headset and/or the one or more ground/reference electrodes (block 1008). The signals may be monitored, analyzed, manipulated, etc. Once the monitoring is complete, the example method 1000 ends (block 1022).

FIG. 11 is a flowchart illustrating an example process of analyzing EEG data (block 1100) collected from the example headset 100 and implemented by the example system 900 of FIG. 9. The example headset 100 has a plurality of electrodes that contact the scalp of a subject to receive electrical signals from the subject's brain. The example process of analyzing EEG data (1100) includes reading the EEG signals from the electrodes (block 1102). In the illustrated example, the signals are converted from an analog signal to a digital signal (block 1104). In some examples, the analog-to-digital conversion takes place in a processing unit, such as, for example, the processing unit 904 of the example system 900. In other examples, the analog-to-digital conversion takes place adjacent the electrodes within the headset to convert the signal as close to the source as possible.

In the illustrated example, the signals are conditioned (block 1106) to improve the usefulness of the signals and the accessibility of the data contained therein. For example, as disclosed above, the conditioning may include amplifying the signals and/or filtering the signals (e.g., with a bandpass filter).

The signals are analyzed (block 1108) to, for example, determine a mental state of the subject, a health condition, an engagement with media as an audience member or effectiveness of the media, an input desire for an electrical device and/or otherwise in accordance with the teachings of this disclosure. For example, the EEG data is analyzed to evaluate brain activity in particular frequency bands of the EEG data and/or in particular regions of the brain. Assessments and/or calculations of the relationship(s) and correlation(s) of the frequency bands and regions of activity of the EEG data are used to determine an emotional or mental state of a person including, for example, attention, emotional engagement, memory or resonance, etc.

For example, the regions of brain activity, the interaction between regions of brain activity, and/or the interactions including couplings between frequency bands signify particular mental states. Also, inter-regional coherencies of frequency band as measured from gain and/or phase may be used to estimate the effectiveness of media in evoking a desired response (e.g., attention) in a person. In addition, inter-hemispheric measurement, asymmetry in one or more frequency bands, asymmetry in inter-regional intra-hemispheric coherence and/or asymmetry in inter-regional intra-hemispheric inter-frequency coupling may be used to measure of emotional engagement.

For example, the signals may be analyzed to determine or calculate an interaction between a first frequency band of the EEG data and a second frequency band of the EEG by detecting a first pattern of oscillation in the first frequency band, detecting a second pattern of oscillation in the second frequency band and identifying a degree of phase synchrony between the first pattern and the second pattern. The analysis may, for example, provide an effectiveness evaluation of media the person observed or consumed when the signals were generated. In this example, the media effectiveness may be based on the degree of phase synchrony.

In other example, the signals may be analyzed to detect a first pattern of oscillation in a first frequency band of EEG data and to detect a second pattern of oscillation in a second frequency band of the EEG data. A degree of phase synchrony is identified between the first pattern from the first frequency band and the second pattern from the second frequency band by detecting a repeating sequence of relative phase angles between the first pattern of oscillation in the first frequency band and the second pattern of oscillation in the second frequency band. The analysis also may, for example, provide an effectiveness evaluation of media the person observed or consumed when the signals were generated. In this example, the media effectiveness evaluation is based on the degree of the phase synchrony at a specific point in time.

In other examples, the signals may be analyzed to determine effectiveness data for media based on a degree of asymmetry between a first frequency band of the EEG data for measured in a first hemisphere of a brain of a panelist and a second frequency band of the EEG data measured in a second hemisphere of the brain. The degree of asymmetry is identified by detecting a first amplitude of the first frequency band and detecting a second amplitude of the second frequency band. The analysis compares the first amplitude and the second amplitude to determine a difference between the first amplitude of the first frequency band and the second amplitude of the second frequency band. The degree of asymmetry is assigned to the relationship between the first frequency band and the second frequency band based on the difference between the first amplitude of the first frequency band and the second amplitude of the second frequency band. Thus, in this example, the effectiveness of the media is based on a degree of inter-frequency, inter-hemispheric asymmetry, which is identified by comparing the amplitudes of two frequency bands from different hemispheres.

In another example, the an interaction between a first frequency band of EEG data and a second frequency band of EEG data of the signals is analyzed by calculating a degree of phase synchrony or amplitude synchrony. The phase synchrony or amplitude synchrony is determined by detecting a first pattern of oscillation in the first frequency band and detecting a second pattern of oscillation in the second frequency band. In addition, a repeating sequence of phase angles or relative amplitude between the first pattern of oscillation in the first frequency band and the second pattern of oscillation in the second frequency band is detected. The effectiveness of the media is based on the interaction.

In still another example, the signals are analyzed to determine effectiveness of media based on a first asymmetry between two amplitudes from two frequency bands and a second asymmetry between two different amplitudes of the frequency bands. Specifically, in this example, the analysis identifies a first asymmetry in two frequency bands of EEG data related to a first portion of the media. The first asymmetry identified by comparing a first amplitude of the first frequency band and a second amplitude of the second frequency band to determine a first difference between the first amplitude of the first frequency band and the second amplitude of the second frequency band. In addition, a first value is assigned to the first asymmetry based on the first difference between the first amplitude of the first frequency band and the second amplitude of the second frequency band. The analysis also includes identifying a second asymmetry in two frequency bands of EEG data related to a second portion of the media. The first and second portions of the media may be temporally disparate portions of the media or different portions that are concurrently experienced by the panelist (e.g., video and audio). The second asymmetry is identified by comparing a third amplitude of the first frequency band and a fourth amplitude of the second frequency band to determine a second difference between the third amplitude of the first frequency band and the fourth amplitude of the second frequency band. A second value is assigned to the second asymmetry based on the second difference between the third amplitude of the first frequency band and the fourth amplitude of the second frequency band. An effectiveness of the media is assessed for each of the first and second portions based on the first value of the first asymmetry and the second value of the second asymmetry.

In the illustrated example, the signals (e.g., the results of the analysis) are transmitted to an output (block 1110), such as, for example, the output 918 of the example system 900. Example modes of output are detailed above including, for example, sounding an alarm, displaying a message and/or other alert on a screen, issuing a report to a local and/or remote computer and/or any other suitable output. In addition, the output may include the wired or wireless communications detailed herein. In some examples, the output includes data reflected of a person paying attention, the person not paying attention, the person in a state of semi-involvement with a media program, or other mental state of the person, and the identity of the program are transmitted to, for example a remote data facility. Raw data, processed data, a history log or an indicator of audience measurement also may be transmitted to the remote data for collection. The remote data facility may be, for example, a marketing company, a broadcast company, an entertainment studio, a television network and/or any other organization that might benefit from or otherwise desire to know when people are and/or are not focused on broadcast programs and what those programs are. This example allows broadcasting companies and/or marketing personnel to analyze which programs people are watching, when they are watching the programs and/or when they are focused during the broadcast. After the output (block 1110), the example process 1100 ends (block 1112).

Figure 12:
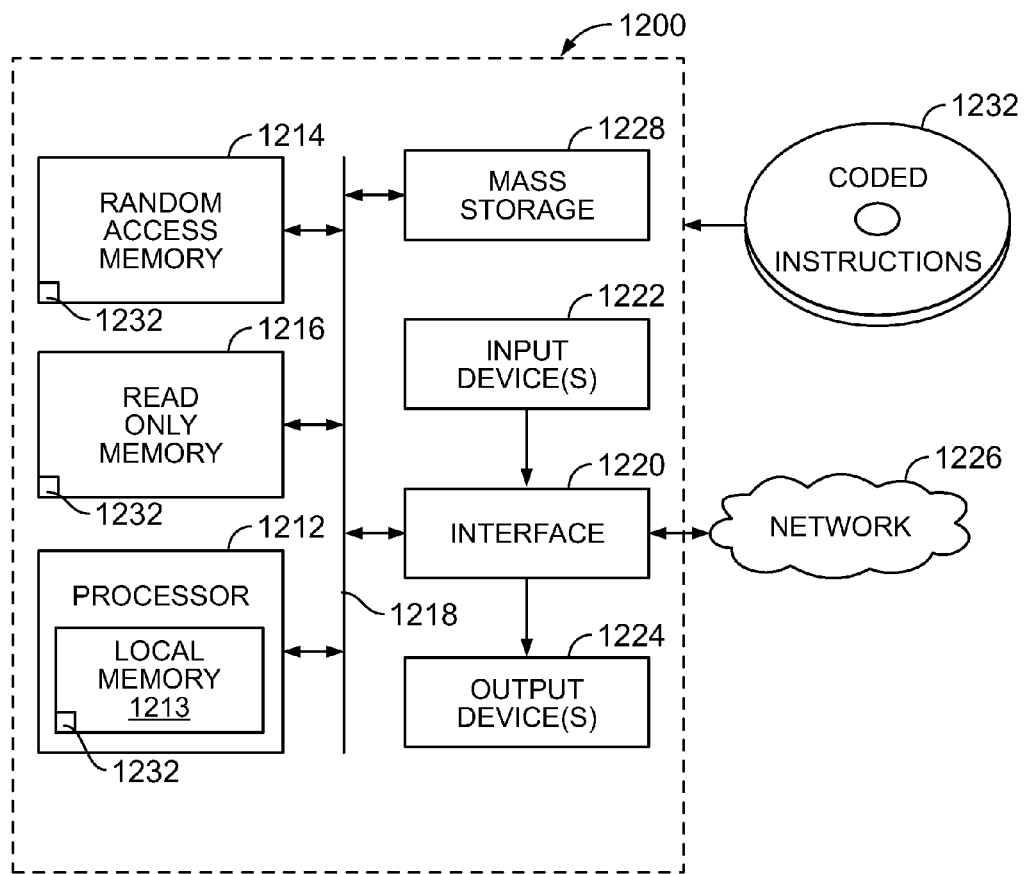
FIG. 12 illustrates an example processor platform that may execute one or more of the instructions of FIGS. 11 and 12 to implement any or all of the example methods, systems and/or apparatus disclosed herein.

FIG. 12 is a block diagram of an example processing platform 1200 capable of executing the one or more of the instructions of FIGS. 10 and 11 to implement one or more portions of the apparatus and/or systems of FIGS. 1A-9. The processing platform 1200 can be, for example, a processor in a headset, a server, a personal computer, a mobile device (e.g., a cell phone, a smart phone, a tablet such as an iPad™), a personal digital assistant (PDA), an Internet appliance and/or any other type of computing device.

The processor platform 1200 of the illustrated example includes a processor 1212. The processor 1212 of the illustrated example is hardware. For example, the processor 1212 can be implemented by one or more integrated circuits, logic circuits, microprocessors or controllers from any desired family or manufacturer.

The processor 1212 of the illustrated example includes a local memory 1213 (e.g., a cache). The processor 1212 of the illustrated example is in communication with a main memory including a volatile memory 1214 and a non-volatile memory 1216 via a bus 1218. The volatile memory 1214 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 1216 may be implemented by flash memory and/or any other desired type of memory device. Access to the main memory 1214, 1216 is controlled by a memory controller.

The processor platform 1200 of the illustrated example also includes an interface circuit 1220. The interface circuit 1220 may be implemented by any type of interface standard, such as an Ethernet interface, a universal serial bus (USB), and/or a PCI express interface.

In the illustrated example, one or more input devices 1222 are connected to the interface circuit 1220. The input device(s) 1222 permit(s) a person to enter data and commands into the processor 1212. The input device(s) can be implemented by, for example, an audio sensor, a microphone, a camera (still or video), a keyboard, a button, a mouse, a touchscreen, a track-pad, a trackball, isopoint and/or a voice recognition system.

One or more output devices 1224 are also connected to the interface circuit 1220 of the illustrated example. The output devices 1224 can be implemented, for example, by display devices (e.g., a light emitting diode (LED), an organic light emitting diode (OLED), a liquid crystal display, a cathode ray tube display (CRT), a touchscreen, a tactile output device and or a light emitting diode (LED). The interface circuit 1220 of the illustrated example, thus, typically includes a graphics driver card, a graphics driver chip or a graphics driver processor.

The interface circuit 1220 of the illustrated example also includes a communication device such as a transmitter, a receiver, a transceiver, a modem and/or network interface card to facilitate exchange of data with external machines (e.g., computing devices of any kind) via a network 1226 (e.g., an Ethernet connection, a digital subscriber line (DSL), a telephone line, coaxial cable, a cellular telephone system, etc.).

The processor platform 1200 of the illustrated example also includes one or more mass storage devices 1228 for storing software and/or data. Examples of such mass storage devices 1228 include floppy disk drives, hard drive disks, compact disk drives, Blu-ray disk drives, RAID systems, and digital versatile disk (DVD) drives.

The coded instructions 1232 of FIGS. 10 and 11 may be stored in the mass storage device 1228, in the volatile memory 1214, in the non-volatile memory 1216, and/or on a removable tangible computer readable storage medium such as a CD or DVD.

Although certain example apparatus have been described herein, the scope of coverage of this patent is not limited thereto. On the contrary, this patent covers all methods, apparatus, and articles of manufacture fairly falling within the scope of the appended claims either literally or under the doctrine of equivalents.

What is claimed is:

1. An apparatus comprising:
a housing having a first end, a second end and an intermediary portion, a wire retainer formed in the intermediary portion;
a first cavity adjacent the first end;
a second cavity adjacent the second end;
a first electrode removably disposed in the first cavity;
a first wire coupled to the first electrode, the first wire releasably retainable in the wire retainer such that the first wire and the wire retainer can be repeatedly coupled and uncoupled to secure the first wire when the first wire and the first electrode are to be coupled to the housing; and
a first magnet disposed in one of the first cavity or the second cavity.

2. The apparatus of claim 1, wherein the intermediary portion is elastically bendable to oppose the first cavity and the second cavity.

3. The apparatus of claim 2, wherein a magnetic force of the first magnet is to secure the apparatus to an ear of a subject.

4. The apparatus of claim 2, wherein the first magnet is to magnetically couple the first end and the second end.

5. The apparatus of claim 2, further including a second magnet or a metallic plate disposed in the other of the first cavity or the second cavity not holding the first magnet, the first magnet magnetically couplable to the second magnet or the metallic plate.

6. The apparatus of claim 5, wherein the second magnet or the metallic plate is disposed between the first electrode and a surface of the first cavity.

7. The apparatus of claim 1, further including a second electrode removably disposed in the second cavity.

8. The apparatus of claim 7, wherein the first electrode is coupled to a first terminal, the second electrode is coupled to a second terminal, and the second terminal is removably coupled to the first terminal.

9. The apparatus of claim 8, wherein the second terminal is magnetically coupled to the first terminal.

10. The apparatus of claim 7, further including a second wire coupled to the second electrode, the second wire releasably retainable in the wire retainer such that the second wire and the wire retainer can be repeatedly coupled and uncoupled to secure the second wire when the second wire and the second electrode are to be coupled to the housing.

11. The apparatus of claim 1, wherein the wire retainer includes a plurality of slits.

12. The apparatus of claim 1, wherein the wire retainer extends into the intermediary portion in a direction that is perpendicular to a longitudinal axis of the intermediary portion.

13. The apparatus of claim 1, wherein the first electrode includes a first flange to couple the first electrode to the first cavity via friction fit.

14. The apparatus of claim 1, further including a headset, the headset including:
- a band to be worn on a head of a subject;
- a strip adjustably coupled to the band, the strip carrying a plurality of electrodes, the strip to be disposed over the head of the subject; and
- a processor communicatively coupled to the electrodes of the strip and the first electrode removably coupled in the first cavity of the housing.

15. The apparatus of claim 14, wherein the first magnet is magnetically couplable to the band to dispose the first electrode against a forehead of the subject.

16. The apparatus of claim 14, wherein the first electrode is coupled to a first terminal via the first wire, the first terminal couplable to the processor to transmit signals gathered by the first electrode to the processor.

17. The apparatus of claim 16, wherein the first terminal is magnetically couplable to the processor.

18. The apparatus of claim 17, wherein the first terminal includes a first magnetic pad and the processor includes a second magnetic pad, the first magnetic pad and the second magnetic pad to engage when the first terminal is coupled to the processor to hold the first terminal on the processor.

19. The apparatus of claim 14, further including a central support supporting the processor, the strip being adjustably coupled to the support.

20. The apparatus of claim 14, wherein the headset further includes a magnetic fastener to couple the strip to the band.

21. The apparatus of claim 20, wherein the magnetic fastener includes:
- a first connector coupled to the band;
- a second magnet or a first metallic plate coupled to the first connector;
- a second connector coupled to the strip; and
- a third magnet or a second metallic plate coupled to the second connector, the second magnet or the first metallic plate and the third magnet or the second metallic plate to couple the first and second connectors.

22. The apparatus of claim 21, wherein the first connector includes an aperture to receive the band, the first connector slidable along the band.

23. The apparatus of claim 22, wherein the first connector includes a leaf spring to engage the band.

24. The apparatus of claim 21, wherein the strip is adjustably coupled to the second connector.

* * * * *